United States Patent [19]
Wheeler et al.

[11] Patent Number: 5,679,509
[45] Date of Patent: Oct. 21, 1997

[54] METHODS AND A DIAGNOSTIC AID FOR DISTINGUISHING A SUBSET OF HPV THAT IS ASSOCIATED WITH AN INCREASED RISK OF DEVELOPING CERVICAL DYSPLASIA AND CERVICAL CANCER

[75] Inventors: Cosette M. Wheeler, Placitas; Cheryl A. Parmenter, Albuquerque, both of N. Mex.

[73] Assignee: University of New Mexico, Albuquerque, N. Mex.

[21] Appl. No.: 316,239

[22] Filed: Sep. 30, 1994

Related U.S. Application Data

[63] Continuation-in-part of Ser. No. 127,906, Sep. 28, 1993, abandoned.
[51] Int. Cl.$^6$ .............................. C12R 1/91; C12Q 1/70
[52] U.S. Cl. .................... 435/5; 435/6; 435/7.21; 435/7.23; 435/91.2; 436/811; 436/813; 436/64
[58] Field of Search .................... 435/6, 5, 7.21, 435/91.2, 7.23; 436/811, 813

[56] References Cited

PUBLICATIONS

Icenogle, et al., Virology, vol. 184, 101–109, 1991.

*Primary Examiner*—Toni R. Scheiner
*Attorney, Agent, or Firm*—Jagtiani & Associates

[57] ABSTRACT

Methods and a diagnostic aid for distinguishing a subset of HPV that is associated with an increased risk of developing cervical dysplasia and cervical cancer. The method comprises either distinguishing leucine or valine at amino acid position 83 in the HPV-16 E6 open reading frame, or detecting a nucleotide of T or G at nt 350 in the HPV-16 E6 gene.

10 Claims, 19 Drawing Sheets

```
LOCUS        PPH16          7904 bp ds-DNA    circular   VRL    18-MAR-1994
DEFINITION   Human papillomavirus type 16 (HPV16), complete genome.
ACCESSION    K02718
KEYWORDS     circular; complete genome.
SOURCE       Papilloma virus type 16 DNA, isolated from a human invasive
             cervical carcinoma.
  ORGANISM   Human papillomavirus type 16
             Viridae; ds-DNA nonenveloped viruses; Papovaviridae.
REFERENCE    1  (bases 1 to 7904)
  AUTHORS    Seedorf,K., Kraemmer,G., Duerst,M., Suhai,S. and Roewekamp,W.G.
  TITLE      Human papillomavirus type 16 DNA sequence
  JOURNAL    Virology 145, 181-185 (1985)
  STANDARD   full automatic
REFERENCE    2  (sites)
  AUTHORS    Kennedy,I.M., Haddow,J.K. and Clements,J.B.
  TITLE      A negative element in the human poapillomavirus type 16 genome acts
             at the level of late mRNA stability
  JOURNAL    J. Virol. 65, 2093-2097 (1991)
  STANDARD   full automatic
COMMENT      The sense strand of this double-stranded circular genome is shown,
             with a numbering system matching the first 60 bp of HPVa1, HPV6b
             and BPV1. The annotation of sites and features is solely based upon
             homology comparison with these other papillomaviruses. In addition
             to the coding sequences reported below, the authors note open
             reading frames which do not start with 'ATG', but which are found
             in other papillomaviruses. In particular, a second portion of the
             E1 gene may be located out to base 2813 (the E1 protein is thought
             to be generally involved in DNA replication).

A potential 'CAT'-box region is found beginning at base 7895 below,
             and 'TATA' boxes for early and late transcripts may be located at
             17, 65 and 4289. Potential polyadenylation signals are at bases
             4213 and 7260.

HPV16, in comparison to HPV types 6 and 11, is more often
             associated with malignant genital cancers in humans.

NCBI gi: 333031
FEATURES             Location/Qualifiers
     source          1..7904
                     /organism="Human papillomavirus type 16"
     TATA_signal     17..23
     TATA_signal     65..71
     CDS             83..559
                     /gene="E6"
                     /note="E6 ORF from 65 to 559; putative; NCBI gi: 333032"
                     /codon_start=1
                     /product="transforming protein"
                     /translation="MHQKRTAMFQDPQERPRKLPQLCTELQTTIHDIILECVYCKQQL
                     LRREVYDFAFRDLCIVYRDGNPYAVCDKCLKFYSKISEYRHYCYSLYGTTLEQQYNKP
                     LCDLLIRCINCQKPLCPEEKQRHLDKKQRFHNIRGRWTGRCMSCCRSSRTRRETQL"
     CDS             562..858
                     /gene="E7"
                     /note="E7 ORF from 544 to 858; putative; NCBI gi: 333033"
                     /codon_start=1
                     /product="transforming protein"
                     /translation="MHGDTPTLHEYMLDLQPETTDLYCYEQLNDSSEEEDEIDGPAGQ
                     AEPDRAHYNIVTFCCKCDSTLRLCVQSTHVDIRTLEDLLMGTLGIVCPICSQKP"
     CDS             join(865..1140,1140..2813)
                     /gene="E1"
```

FIG. 2A

```
                    /note="E1 interrupted ORF from 859 to 2813; putative;
                    NCBI gi: 459912"
                    /codon_start=1
                    /product="replication protein"
                    /translation="MADPAGTNGEEGTGCNGWFYVEAVVEKKTGDAISDDENENDSDT
                    GEDLVDFIVNDNDYLTQAETETAHALFTAQEAKQHRDAVQVLKRKYLVSPLSDISGCV
                    DNNISPRLKAICIEKQSRAAKRRLFESEDSGYGNTEVETQQMLQVEGRHETETPCSQY
                    SGGSGGGCSQYSSGSGGEGVSERHTICQTPLTNILNVLKTSNAKAAMLAKFKELYGVS
                    FSELVRPFKSNKSTCCDWCIAAFGLTPSIADSIKTLLQQYCLYLHIQSLACSWGMVVL
                    LLVRYKCGKNRETIEKLLSKLLCVSPMCMMIEPPKLRSTAAALYWYKTGISNISEVYG
                    DTPEWIQRQTVLQHSFNDCTFELSQMVQWAYDNDIVDDSEIAYKYAQLADTNSNASAF
                    LKSNSQAKIVKDCATMCRHYKRAEKKQMSMSQWIKYRCDRVDDGGDWKQIVMFLRYQG
                    VEFMSFLTALKRFLQGIPKKNCILLYGAANTGKSLFGMSLMKFLQGSVICFVNSKSHF
                    WLQPLADAKIGMLDDATVPCWNYIDDNLRNALDGNLVSMDVKHRPLVQLKCPPLLITS
                    NINAGTDSRWPYLHNRLVVFTFPNEFPFDENGNPVYELNDKNWKSFFSRTWSRLSLHE
                    DEDKENDGDSLPTFKCVSGQNTNTL"
CDS                 2755..3852
                    /gene="E2"
                    /note="E2 ORF from 2725 to 3852; putative;  NCBI gi:
                    333035"
                    /codon_start=1
                    /product="regulatory protein"
                    /translation="METLCQRLNVCQDKILTHYENDSTDLRDHIDYWKHMRLECAIYY
                    KAREMGFKHINHQVVPTLAVSKNKALQAIELQLTLETIYNSQYSNEKWTLQDVSLEVY
                    LTAPTGCIKKHGYTVEVQFDGDICNTMHYTNWTHIYICEEASVTVVEGQVDYYGLYYV
                    HEGIRTYFVQFKDDAEKYSKNKVWEVHAGGQVILCPTSVFSSNEVSSPEIIRQHLANH
                    PAATHTKAVALGTEETQTTIQRPRSEPDTGNPCHTTKLLHRDSVDSAPILTAFNSSHK
                    GRINCNSNTTPIVHLKGDANTLKCLRYRFKKHCTLYTAVSSTWHWTGHNVKHKSAIVT
                    LTYDSEWQRDQFLSQVKIPKTITVSTGFMSI"
CDS                 <3332..3619
                    /gene="E4"
                    /note="E4 ORF from 3332 to 3619;  putative;  NCBI gi:
                    459913"
                    /codon_start=1
                    /translation="YYVLHLCLAATKYPLLKLLGSTWPTTPPRPIPKPSPWAPKKHRR
                    LSSDQDQSQTPETPATPLSCCTETQWTVLQSSLHLTAHTKDGLTVIVTLHP"
CDS                 <3863..4099
                    /gene="E5"
                    /note="E5 ORF from 3863 to 4099;  putative;  NCBI gi:
                    459914"
                    /codon_start=1
                    /translation="YCIHNITGVLFALLCVLLCVCLLIRPLLLSVSTYTSLIILVLLL
                    WITAASAFRCFIVYIIFVYIPLFLIHTHARFLIT"
polyA_signal        4213..4218
                    /note="putative"
CDS                 4235..5656
                    /gene="L2"
                    /note="L2 ORF from 4133 to 5656; putative;  NCBI gi:
                    333036"
                    /codon_start=1
                    /product="minor capsid protein"
                    /translation="MRHKRSAKRTKRASATQLYKTCKQAGTCPPDIIPKVEGKTIAEQ
                    ILQYGSMGVFFGGLGIGTGSGTGGRTGYIPLGTRPPTATDTLAPVRPPLTVDPVGPSD
                    PSIVSLVEETSFIDAGAPTSVPSIPPDVSGFSITTSTDTTPAILDINNTVTTVTTHNN
                    PTFTDPSVLQPPTPAETGGHFTLSSSTISTHNYEEIPMDTFIVSTNPNTVTSSTPIPG
                    SRPVARLGLYSRTTQQVKVVDPAFVTTPTKLITYDNPAYEGIDVDNTLYFSSNDNSIN
                    IAPDPDFLDIVALHRPALTSRRTGIRYSRIGNKQTLRTRSGKSIGAKVHYYYDLSTID
                    PAEEIELQTITPSTYTTTSHAASPTSINNGLYDIYADDFITDTSTTPVPSVPSTSLSG
                    YIPANTTIPFGGAYNIPLVSGPDIPINITDQAPSLIPIVPGSPQYTIIADAGDFYLHP
                    SYYMLRKRRKRLPYFFSDVSLAA"
```

FIG. 2B

```
   TATA_signal    4289..4295
   CDS            5559..7154
                  /gene="L1"
                  /note="L1 ORF from 5526 to 7154; putative; NCBI gi:
                  333037"
                  /codon_start=1
                  /product="major capsid protein"
                  /translation="MQVTFIYILVITCYENDVNVYHIFFQMSLWLPSEATVYLPPVPV
                  SKVVSTDEYVARTNIYYHAGTSRLLAVGHPYFPIKKPNNNKILVPKVSGLQYRVFRIH
                  LPDPNKFGFPDTSFYNPDTQRLVWACVGVEVGRGQPLGVGISGHPLLNKLDDTENASA
                  YAANAGVDNRECISMDYKQTQLCLIGCKPPIGEHWGKGSPCTNVAVNPGDCPPLELIN
                  TVIQDGDMVHTGFGAMDFTTLQANKSEVPLDICTSICKYPDYIKMVSEPYGDSLFFYL
                  RREQMFVRHLFNRAGTVGENVPDDLYIKGSGSTANLASSNYFPTPSGSMVTSDAQIFN
                  KPYWLQRAQGHNNGICWGNQLFVTVVDTTRSTNMSLCAAISTSETTYKNTNFKEYLRH
                  GEEYDLQFIFQLCKITLTADVMTYIHSMNSTILEDWNFGLQPPPGGTLEDTYRFVTQA
                  IACQKHTPPAPKEDDPLKKYTFWEVNLKEKFSADLDQFPLGRKFLLQAGLKAKPKFTL
                  GKRKATPTTSSTSTTAKRKKRKL"
   polyA_signal   7260..7265
BASE COUNT     2601 a   1377 c   1509 g   2417 t
ORIGIN         Unreported.

Pph16  Length: 7904  September 7, 1994  17:18  Type: N  Check: 6074  ..

1  ACTACAATAA TTCATGTATA AAACTAAGGG CGTAACCGAA ATCGGTTGAA

51  CCGAAACCGG TTAGTATAAA AGCAGACATT TTATGCACCA AAAGAGAACT

101  GCAATGTTTC AGGACCCACA GGAGCGACCC AGAAAGTTAC CACAGTTATG

151  CACAGAGCTG CAAACAACTA TACATGATAT AATATTAGAA TGTGTGTACT

201  GCAAGCAACA GTTACTGCGA CGTGAGGTAT ATGACTTTGC TTTTCGGGAT

251  TTATGCATAG TATATAGAGA TGGGAATCCA TATGCTGTAT GTGATAAATG

301  TTTAAAGTTT TATTCTAAAA TTAGTGAGTA TAGACATTAT TGTTATAGTT

351  TGTATGGAAC AACATTAGAA CAGCAATACA ACAAACCGTT GTGTGATTTG

401  TTAATTAGGT GTATTAACTG TCAAAAGCCA CTGTGTCCTG AAGAAAAGCA

451  AAGACATCTG GACAAAAAGC AAAGATTCCA TAATATAAGG GGTCGGTGGA

501  CCGGTCGATG TATGTCTTGT TGCAGATCAT CAAGAACACG TAGAGAAACC

551  CAGCTGTAAT CATGCATGGA GATACACCTA CATTGCATGA ATATATGTTA

601  GATTTGCAAC CAGAGACAAC TGATCTCTAC TGTTATGAGC AATTAAATGA

651  CAGCTCAGAG GAGGAGGATG AAATAGATGG TCCAGCTGGA CAAGCAGAAC

701  CGGACAGAGC CCATTACAAT ATTGTAACCT TTTGTTGCAA GTGTGACTCT

751  ACGCTTCGGT TGTGCGTACA AAGCACACAC GTAGACATTC GTACTTTGGA

801  AGACCTGTTA ATGGGCACAC TAGGAATTGT GTGCCCCATC TGTTCTCAGA

851  AACCATAATC TACCATGGCT GATCCTGCAG GTACCAATGG GGAAGAGGGT

901  ACGGGATGTA ATGGATGGTT TTATGTAGAG GCTGTAGTGG AAAAAAAAAC
```

FIG. 2C

```
 951  AGGGGATGCT ATATCAGATG ACGAGAACGA AAATGACAGT GATACAGGTG
1001  AAGATTTGGT AGATTTTATA GTAAATGATA ATGATTATTT AACACAGGCA
1051  GAAACAGAGA CAGCACATGC GTTGTTTACT GCACAGGAAG CAAAACAACA
1101  TAGAGATGCA GTACAGGTTC TAAAACGAAA GTATTTGGTA GTCCACTTAG
1151  TGATATTAGT GGATGTGTAG ACAATAATAT TAGTCCTAGA TTAAAAGCTA
1201  TATGTATAGA AAAACAAAGT AGAGCTGCAA AAGGAGATT ATTTGAAAGC
1251  GAAGACAGCG GTATGGCAA TACTGAAGTG GAAACTCAGC AGATGTTACA
1301  GGTAGAAGGG CGCCATGAGA CTGAAACACC ATGTAGTCAG TATAGTGGTG
1351  GAAGTGGGGG TGGTTGCAGT CAGTACAGTA GTGGAAGTGG GGGAGAGGGT
1401  GTTAGTGAAA GACACACTAT ATGCCAAACA CCACTTACAA ATATTTTAAA
1451  TGTACTAAAA ACTAGTAATG CAAAGGCAGC AATGTTAGCA AAATTTAAAG
1501  AGTTATACGG GGTGAGTTTT TCAGAATTAG TAAGACCATT TAAAAGTAAT
1551  AAATCAACGT GTTGCGATTG GTGTATTGCT GCATTTGGAC TTACACCCAG
1601  TATAGCTGAC AGTATAAAAA CACTATTACA ACAATATTGT TTATATTTAC
1651  ACATTCAAAG TTTAGCATGT TCATGGGGAA TGGTTGTGTT ACTATTAGTA
1701  AGATATAAAT GTGGAAAAAA TAGAGAAACA ATTGAAAAAT TGCTGTCTAA
1751  ACTATTATGT GTGTCTCCAA TGTGTATGAT GATAGAGCCT CCAAAATTGC
1801  GTAGTACAGC AGCAGCATTA TATTGGTATA AACAGGTAT ATCAAATATT
1851  AGTGAAGTGT ATGGAGACAC GCCAGAATGG ATACAAAGAC AAACAGTATT
1901  ACAACATAGT TTTAATGATT GTACATTTGA ATTATCACAG ATGGTACAAT
1951  GGGCCTACGA TAATGACATA GTAGACGATA GTGAAATTGC ATATAAATAT
2001  GCACAATTGG CAGACACTAA TAGTAATGCA AGTGCCTTTC TAAAAAGTAA
2051  TTCACAGGCA AAAATTGTAA AGGATTGTGC AACAATGTGT AGACATTATA
2101  AACGAGCAGA AAAAAAACAA ATGAGTATGA GTCAATGGAT AAAATATAGA
2151  TGTGATAGGG TAGATGATGG AGGTGATTGG AAGCAAATTG TTATGTTTTT
2201  AAGGTATCAA GGTGTAGAGT TTATGTCATT TTTAACTGCA TTAAAAAGAT
2251  TTTTGCAAGG CATACCTAAA AAAAATTGCA TATTACTATA TGGTGCAGCT
2301  AACACAGGTA AATCATTATT TGGTATGAGT TTAATGAAAT TTCTGCAAGG
2351  GTCTGTAATA TGTTTTGTAA ATTCTAAAAG CCATTTTTGG TTACAACCAT
2401  TAGCAGATGC CAAAATAGGT ATGTTAGATG ATGCTACAGT GCCCTGTTGG
```

FIG. 2D

2451 AACTACATAG ATGACAATTT AAGAAATGCA TTGGATGGAA ATTTAGTTTC

2501 TATGGATGTA AAGCATAGAC CATTGGTACA ACTAAAATGC CCTCCATTAT

2551 TAATTACATC TAACATTAAT GCTGGTACAG ATTCTAGGTG GCCTTATTTA

2601 CATAATAGAT TGGTGGTGTT TACATTTCCT AATGAGTTTC CATTTGACGA

2651 AAACGGAAAT CCAGTGTATG AGCTTAATGA TAAGAACTGG AAATCCTTTT

2701 TCTCAAGGAC GTGGTCCAGA TTAAGTTTGC ACGAGGACGA GGACAAGGAA

2751 AACGATGGAG ACTCTTTGCC AACGTTTAAA TGTGTGTCAG GACAAAATAC

2801 TAACACATTA TGAAAATGAT AGTACAGACC TACGTGACCA TATAGACTAT

2851 TGGAAACACA TGCGCCTAGA ATGTGCTATT TATTACAAGG CCAGAGAAAT

2901 GGGATTTAAA CATATTAACC ACCAAGTGGT GCCAACACTG GCTGTATCAA

2951 AGAATAAAGC ATTACAAGCA ATTGAACTGC AACTAACGTT AGAAACAATA

3001 TATAACTCAC AATATAGTAA TGAAAGTGG ACATTACAAG ACGTTAGCCT

3051 TGAAGTGTAT TTAACTGCAC AACAGGATG TATAAAAAAA CATGGATATA

3101 CAGTGGAAGT GCAGTTTGAT GGAGACATAT GCAATACAAT GCATTATACA

3151 AACTGGACAC ATATATATAT TTGTGAAGAA GCATCAGTAA CTGTGGTAGA

3201 GGGTCAAGTT GACTATTATG GTTTATATTA TGTTCATGAA GGAATACGAA

3251 CATATTTTGT GCAGTTTAAA GATGATGCAG AAAAATATAG TAAAAATAAA

3301 GTATGGGAAG TTCATGCGGG TGGTCAGGTA ATATTATGTC CTACATCTGT

3351 GTTTAGCAGC AACGAAGTAT CCTCTCCTGA AATTATTAGG CAGCACTTGG

3401 CCAACCACCC CGCCGCGACC CATACCAAAG CCGTCGCCTT GGGCACCGAA

3451 GAAACACAGA CGACTATCCA GCGACCAAGA TCAGAGCCAG ACACCGGAAA

3501 CCCCTGCCAC ACCACTAAGT TGTTGCACAG AGACTCAGTG GACAGTGCTC

3551 CAATCCTCAC TGCATTTAAC AGCTCACACA AAGGACGGAT TAACTGTAAT

3601 AGTAACACTA CACCCATAGT ACATTTAAAA GGTGATGCTA ATACTTTAAA

3651 ATGTTTAAGA TATAGATTTA AAAAGCATTG TACATTGTAT ACTGCAGTGT

3701 CGTCTACATG GCATTGGACA GGACATAATG TAAAACATAA AAGTGCAATT

3751 GTTACACTTA CATATGATAG TGAATGGCAA CGTGACCAAT TTTTGTCTCA

3801 AGTTAAAATA CCAAAAACTA TTACAGTGTC TACTGGATTT ATGTCTATAT

3851 GACAAATCTT GATACTGCAT CCACAACATT ACTGGCGTGC TTTTTGCTTT

3901 GCTTTGTGTG CTTTTGTGTG TCTGCCTATT AATACGTCCG CTGCTTTTGT

FIG. 2E

```
3951  CTGTGTCTAC ATACACATCA TTAATAATAT TGGTATTACT ATTGTGGATA
4001  ACAGCAGCCT CTGCGTTTAG GTGTTTTATT GTATATATTA TATTTGTTTA
4051  TATACCATTA TTTTTAATAC ATACACATGC ACGCTTTTTA ATTACATAAT
4101  GTATATGTAC ATAATGTAAT TGTTACATAT AATTGTTGTA TACCATAACT
4151  TACTATTTTT TCTTTTTTAT TTTCATATAT AATTTTTTTT TTTGTTTGTT
4201  TGTTTGTTTT TTAATAAACT GTTATTACTT AACAATGCGA CACAAACGTT
4251  CTGCAAAACG CACAAAACGT GCATCGGCTA CCCAACTTTA TAAAACATGC
4301  AAACAGGCAG GTACATGTCC ACCTGACATT ATACCTAAGG TTGAAGGCAA
4351  AACTATTGCT GAACAAATAT TACAATATGG AAGTATGGGT GTATTTTTTG
4401  GTGGGTTAGG AATTGGAACA GGGTCGGGTA CAGGCGGACG CACTGGGTAT
4451  ATTCCATTGG GAACAAGGCC TCCCACAGCT ACAGATACAC TTGCTCCTGT
4501  AAGACCCCCT TTAACAGTAG ATCCTGTGGG CCCTTCTGAT CCTTCTATAG
4551  TTTCTTTAGT GGAAGAAACT AGTTTTATTG ATGCTGGTGC ACCAACATCT
4601  GTACCTTCCA TTCCCCCAGA TGTATCAGGA TTTAGTATTA CTACTTCAAC
4651  TGATACCACA CCTGCTATAT TAGATATTAA TAATACTGTT ACTACTGTTA
4701  CTACACATAA TAATCCCACT TTCACTGACC CATCTGTATT GCAGCCTCCA
4751  ACACCTGCAG AAACTGGAGG GCATTTTACA CTTTCATCAT CCACTATTAG
4801  TACACATAAT TATGAAGAAA TTCCTATGGA TACATTTATT GTTAGCACAA
4851  ACCCTAACAC AGTAACTAGT AGCACACCCA TACCAGGGTC TCGCCCAGTG
4901  GCACGCCTAG GATTATATAG TCGCACAACA CAACAGGTTA AGTTGTAGA
4951  CCCTGCTTTT GTAACCACTC CCACTAAACT TATTACATAT GATAATCCTG
5001  CATATGAAGG TATAGATGTG GATAATACAT TATATTTTTC TAGTAATGAT
5051  AATAGTATTA ATATAGCTCC AGATCCTGAC TTTTTGGATA TAGTTGCTTT
5101  ACATAGGCCA GCATTAACCT CTAGGCGTAC TGGCATTAGG TACAGTAGAA
5151  TTGGTAATAA ACAAACACTA CGTACTCGTA GTGGAAAATC TATAGGTGCT
5201  AAGGTACATT ATTATTATGA TTTAAGTACT ATTGATCCTG CAGAAGAAAT
5251  AGAATTACAA ACTATAACAC CTTCTACATA TACTACCACT TCACATGCAG
5301  CCTCACCTAC TTCTATTAAT AATGGATTAT ATGATATTTA TGCAGATGAC
5351  TTTATTACAG ATACTTCTAC AACCCCGGTA CCATCTGTAC CCTCTACATC
5401  TTTATCAGGT TATATTCCTG CAAATACAAC AATTCCTTTT GGTGGTGCAT
```

FIG. 2F

```
5451  ACAATATTCC TTTAGTATCA GGTCCTGATA TACCCATTAA TATAACTGAC
5501  CAAGCTCCTT CATTAATTCC TATAGTTCCA GGGTCTCCAC AATATACAAT
5551  TATTGCTGAT GCAGGTGACT TTTATTTACA TCCTAGTTAT TACATGTTAC
5601  GAAAACGACG TAAACGTTTA CCATATTTTT TTTCAGATGT CTCTTTGGCT
5651  GCCTAGTGAG GCCACTGTCT ACTTGCCTCC TGTCCCAGTA TCTAAGGTTG
5701  TAAGCACGGA TGAATATGTT GCACGCACAA ACATATATTA TCATGCAGGA
5751  ACATCCAGAC TACTTGCAGT TGGACATCCC TATTTTCCTA TTAAAAAACC
5801  TAACAATAAC AAAATATTAG TTCCTAAAGT ATCAGGATTA CAATACAGGG
5851  TATTTAGAAT ACATTTACCT GACCCCAATA AGTTTGGTTT TCCTGACACC
5901  TCATTTTATA ATCCAGATAC ACAGCGGCTG GTTTGGGCCT GTGTAGGTGT
5951  TGAGGTAGGT CGTGGTCAGC CATTAGGTGT GGGCATTAGT GGCCATCCTT
6001  TATTAAATAA ATTGGATGAC ACAGAAAATG CTAGTGCTTA TGCAGCAAAT
6051  GCAGGTGTGG ATAATAGAGA ATGTATATCT ATGGATTACA AACAAACACA
6101  ATTGTGTTTA ATTGGTTGCA AACCACCTAT AGGGGAACAC TGGGGCAAAG
6151  GATCCCCATG TACCAATGTT GCAGTAAATC CAGGTGATTG TCCACCATTA
6201  GAGTTAATAA ACACAGTTAT TCAGGATGGT GATATGGTTC ATACTGGCTT
6251  TGGTGCTATG GACTTTACTA CATTACAGGC TAACAAAAGT GAAGTTCCAC
6301  TGGATATTTG TACATCTATT TGCAAATATC CAGATTATAT TAAAATGGTG
6351  TCAGAACCAT ATGGCGACAG CTTATTTTTT TATTTACGAA GGGAACAAAT
6401  GTTTGTTAGA CATTTATTTA ATAGGGCTGG TACTGTTGGT GAAAATGTAC
6451  CAGACGATTT ATACATTAAA GGCTCTGGGT CTACTGCAAA TTTAGCCAGT
6501  TCAAATTATT TTCCTACACC TAGTGGTTCT ATGGTTACCT CTGATGCCCA
6551  AATATTCAAT AAACCTTATT GGTTACAACG AGCACAGGGC CACAATAATG
6601  GCATTTGTTG GGGTAACCAA CTATTTGTTA CTGTTGTTGA TACTACACGC
6651  AGTACAAATA TGTCATTATG TGCTGCCATA TCTACTTCAG AAACTACATA
6701  TAAAAATACT AACTTTAAGG AGTACCTACG ACATGGGGAG GAATATGATT
6751  TACAGTTTAT TTTTCAACTG TGCAAAATAA CCTTAACTGC AGACGTTATG
6801  ACATACATAC ATTCTATGAA TTCCACTATT TTGGAGGACT GGAATTTTGG
6851  TCTACAACCT CCCCCAGGAG GCACACTAGA AGATACTTAT AGGTTTGTAA
6901  CCCAGGCAAT TGCTTGTCAA AAACATACAC CTCCAGCACC TAAAGAAGAT
```

FIG. 2G

```
6951  GATCCCCTTA AAAAATACAC TTTTTGGGAA GTAAATTTAA AGGAAAAGTT
7001  TTCTGCAGAC CTAGATCAGT TTCCTTTAGG ACGCAAATTT TTACTACAAG
7051  CAGGATTGAA GGCCAAACCA AAATTTACAT TAGGAAAACG AAAAGCTACA
7101  CCCACCACCT CATCTACCTC TACAACTGCT AAACGCAAAA AACGTAAGCT
7151  GTAAGTATTG TATGTATGTT GAATTAGTGT TGTTTGTTGT GTATATGTTT
7201  GTATGTGCTT GTATGTGCTT GTAAATATTA AGTTGTATGT GTGTTTGTAT
7251  GTATGGTATA ATAAACACGT GTGTATGTGT TTTTAAATGC TTGTGTAACT
7301  ATTGTGTCAT GCAACATAAA TAAACTTATT GTTTCAACAC CTACTAATTG
7351  TGTTGTGGTT ATTCATTGTA TATAAACTAT ATTTGCTACA TCCTGTTTTT
7401  GTTTTATATA TACTATATTT TGTAGCGCCA GGCCCATTTT GTAGCTTCAA
7451  CCGAATTCGG TTGCATGCTT TTTGGCACAA AATGTGTTTT TTTAAATAGT
7501  TCTATGTCAG CAACTATGGT TTAAACTTGT ACGTTCCTG CTTGCCATGC
7551  GTGCCAAATC CCTGTTTTCC TGACCTGCAC TGCTTGCCAA CCATTCCATT
7601  GTTTTTTACA CTGCACTATG TGCAACTACT GAATCACTAT GTACATTGTG
7651  TCATATAAAA TAAATCACTA TGCGCCAACG CCTTACATAC CGCTGTTAGG
7701  CACATATTTT TGGCTTGTTT TAACTAACCT AATTGCATAT TTGGCATAAG
7751  GTTTAAACTT CTAAGGCCAA CTAAATGTCA CCCTAGTTCA TACATGAACT
7801  GTGTAAAGGT TAGTCATACA TTGTTCATTT GTAAAACTGC ACATGGGTGT
7851  GTGCAAACCG ATTTTGGGTT ACACATTTAC AAGCAACTTA TATAATAATA
7901  CTAA
```

FIG. 2H

```
LOCUS       PPH16         7904 bp ds-DNA    circular   VRL       18-MAR-1994
DEFINITION  Human papillomavirus type 16 (HPV16), complete genome.
ACCESSION   K02718
KEYWORDS    circular; complete genome.
SOURCE      Papilloma virus type 16 DNA, isolated from a human invasive
            cervical carcinoma.
  ORGANISM  Human papillomavirus type 16
            Viridae; ds-DNA nonenveloped viruses; Papovaviridae.
REFERENCE   1  (bases 1 to 7904)
  AUTHORS   Seedorf,K., Kraemmer,G., Duerst,M., Suhai,S. and Roewekamp,W.G.
  TITLE     Human papillomavirus type 16 DNA sequence
  JOURNAL   Virology 145, 181-185 (1985)
  STANDARD  full automatic
REFERENCE   2  (sites)
  AUTHORS   Kennedy,I.M., Haddow,J.K. and Clements,J.B.
  TITLE     A negative element in the human poapillomavirus type 16 genome acts
            at the level of late mRNA stability
  JOURNAL   J. Virol. 65, 2093-2097 (1991)
  STANDARD  full automatic
COMMENT     The sense strand of this double-stranded circular genome is shown,
            with a numbering system matching the first 60 bp of HPVa1, HPV6b
            and BPV1. The annotation of sites and features is solely based upon
            homology comparison with these other papillomaviruses. In addition
            to the coding sequences reported below, the authors note open
            reading frames which do not start with 'ATG', but which are found
            in other papillomaviruses. In particular, a second portion of the
            E1 gene may be located out to base 2813 (the E1 protein is thought
            to be generally involved in DNA replication).

A potential 'CAT'-box region is found beginning at base 7895 below,
            and 'TATA' boxes for early and late transcripts may be located at
            17, 65 and 4289. Potential polyadenylation signals are at bases
            4213 and 7260.

HPV16, in comparison to HPV types 6 and 11, is more often
            associated with malignant genital cancers in humans.

NCBI gi: 333031
FEATURES             Location/Qualifiers
     source          1..7904
                     /organism="Human papillomavirus type 16"
     TATA_signal     17..23
     TATA_signal     65..71
     CDS             83..559
                     /gene="E6"
                     /note="E6 ORF from 65 to 559; putative;  NCBI gi: 333032"
                     /codon_start=1
                     /product="transforming protein"
                     /translation="MHQKRTAMFQDPQERPRKLPQLCTELQTTIHDIILECVYCKQQL
                     LRREVYDFAFRDLCIVYRDGNPYAVCDKCLKFYSKISEYRHYCYSLYGTTLEQQYNKP
                     LCDLLIRCINCQKPLCPEEKQRHLDKKQRFHNIRGRWTGRCMSCCRSSRTRRETQL"
     CDS             562..858
                     /gene="E7"
                     /note="E7 ORF from 544 to 858; putative;  NCBI gi: 333033"
                     /codon_start=1
                     /product="transforming protein"
                     /translation="MHGDTPTLHEYMLDLQPETTDLYCYEQLNDSSEEEDEIDGPAGQ
                     AEPDRAHYNIVTFCCKCDSTLRLCVQSTHVDIRTLEDLLMGTLGIVCPICSQKP"
     CDS             join(865..1140,1140..2813)
                     /gene="E1"
```

FIG. 3A

```
                    /note="E1 interrupted ORF from 859 to 2813; putative;
                    NCBI gi: 459912"
                    /codon_start=1
                    /product="replication protein"
                    /translation="MADPAGTNGEEGTGCNGWFYVEAVVEKKTGDAISDDENENDSDT
                    GEDLVDFIVNDNDYLTQAETETAHALFTAQEAKQHRDAVQVLKRKYLVSPLSDISGCV
                    DNNISPRLKAICIEKQSRAAKRRLFESEDSGYGNTEVETQQMLQVEGRHETETPCSQY
                    SGGSGGGCSQYSSGSGGEGVSERHTICQTPLTNILNVLKTSNAKAAMLAKFKELYGVS
                    FSELVRPFKSNKSTCCDWCIAAFGLTPSIADSIKTLLQQYCLYLHIQSLACSWGMVVL
                    LLVRYKCGKNRETIEKLLSKLLCVSPMCMMIEPPKLRSTAAALYWYKTGISNISEVYG
                    DTPEWIQRQTVLQHSFNDCTFELSQMVQWAYDNDIVDDSEIAYKYAQLADTNSNASAF
                    LKSNSQAKIVKDCATMCRHYKRAEKKQMSMSQWIKYRCDRVDDGGDWKQIVMFLRYQG
                    VEFMSFLTALKRFLQGIPKKNCILLYGAANTGKSLFGMSLMKFLQGSVICFVNSKSHF
                    WLQPLADAKIGMLDDATVPCWNYIDDNLRNALDGNLVSMDVKHRPLVQLKCPPLLITS
                    NINAGTDSRWPYLHNRLVVFTFPNEFPFDENGNPVYELNDKNWKSFFSRTWSRLSLHE
                    DEDKENDGDSLPTFKCVSGQNTNTL"
CDS                 2755..3852
                    /gene="E2"
                    /note="E2 ORF from 2725 to 3852; putative; NCBI gi:
                    333035"
                    /codon_start=1
                    /product="regulatory protein"
                    /translation="METLCQRLNVCQDKILTHYENDSTDLRDHIDYWKHMRLECAIYY
                    KAREMGFKHINHQVVPTLAVSKNKALQAIELQLTLETIYNSQYSNEKWTLQDVSLEVY
                    LTAPTGCIKKHGYTVEVQFDGDICNTMHYTNWTHIYICEEASVTVVEGQVDYYGLYYV
                    HEGIRTYFVQFKDDAEKYSKNKVWEVHAGGQVILCPTSVFSSNEVSSPEIIRQHLANH
                    PAATHTKAVALGTEETQTTIQRPRSEPDTGNPCHTTKLLHRDSVDSAPILTAFNSSHK
                    GRINCNSNTTPIVHLKGDANTLKCLRYRFKKHCTLYTAVSSTWHWTGHNVKHKSAIVT
                    LTYDSEWQRDQFLSQVKIPKTITVSTGFMSI"
CDS                 <3332..3619
                    /gene="E4"
                    /note="E4 ORF from 3332 to 3619; putative; NCBI gi:
                    459913"
                    /codon_start=1
                    /translation="YYVLHLCLAATKYPLLKLLGSTWPTTPPRPIPKPSPWAPKKHRR
                    LSSDQDQSQTPETPATPLSCCTETQWTVLQSSLHLTAHTKDGLTVIVTLHP"
CDS                 <3863..4099
                    /gene="E5"
                    /note="E5 ORF from 3863 to 4099; putative; NCBI gi:
                    459914"
                    /codon_start=1
                    /translation="YCIHNITGVLFALLCVLLCVCLLIRPLLLSVSTYTSLIILVLLL
                    WITAASAFRCFIVYIIFVYIPLFLIHTHARFLIT"
polyA_signal        4213..4218
                    /note="putative"
CDS                 4235..5656
                    /gene="L2"
                    /note="L2 ORF from 4133 to 5656; putative; NCBI gi:
                    333036"
                    /codon_start=1
                    /product="minor capsid protein"
                    /translation="MRHKRSAKRTKRASATQLYKTCKQAGTCPPDIIPKVEGKTIAEQ
                    ILQYGSMGVFFGGLGIGTGSGTGGRTGYIPLGTRPPTATDTLAPVRPPLTVDPVGPSD
                    PSIVSLVEETSFIDAGAPTSVPSIPPDVSGFSITTSTDTTPAILDINNTVTTVTTHNN
                    PTFTDPSVLQPPTPAETGGHFTLSSSTISTHNYEEIPMDTFIVSTNPNTVTSSTPIPG
                    SRPVARLGLYSRTTQQVKVVDPAFVTTPTKLITYDNPAYEGIDVDNTLYFSSNDNSIN
                    IAPDPDFLDIVALHRPALTSRRTGIRYSRIGNKQTLRTRSGKSIGAKVHYYYDLSTID
                    PAEEIELQTITPSTYTTTSHAASPTSINNGLYDIYADDFITDTSTTPVPSVPSTSLSG
                    YIPANTTIPFGGAYNIPLVSGPDIPINITDQAPSLIPIVPGSPQYTIIADAGDFYLHP
                    SYYMLRKRRKRLPYFFSDVSLAA"
```

FIG. 3B

```
     TATA_signal      4289..4295
     CDS              5559..7154
                      /gene="L1"
                      /note="L1 ORF from 5526 to 7154; putative;  NCBI gi:
                      333037"
                      /codon_start=1
                      /product="major capsid protein"
                      /translation="MQVTFIYILVITCYENDVNVYHIFFQMSLWLPSEATVYLPPVPV
                      SKVVSTDEYVARTNIYYHAGTSRLLAVGHPYFPIKKPNNNKILVPKVSGLQYRVFRIH
                      LPDPNKFGFPDTSFYNPDTQRLVWACVGVEVGRGQPLGVGISGHPLLNKLDDTENASA
                      YAANAGVDNRECISMDYKQTQLCLIGCKPPIGEHWGKGSPCTNVAVNPGDCPPLELIN
                      TVIQDGDMVHTGFGAMDFTTLQANKSEVPLDICTSICKYPDYIKMVSEPYGDSLFFYL
                      RREQMFVRHLFNRAGTVGENVPDDLYIKGSGSTANLASSNYFPTPSGSMVTSDAQIFN
                      KPYWLQRAQGHNNGICWGNQLFVTVVDTTRSTNMSLCAAISTSETTYKNTNFKEYLRH
                      GEEYDLQFIFQLCKITLTADVMTYIHSMNSTILEDWNFGLQPPPGGTLEDTYRFVTQA
                      IACQKHTPPAPKEDDPLKKYTFWEVNLKEKFSADLDQFPLGRKFLLQAGLKAKPKFTL
                      GKRKATPTTSSTSTTAKRKKRKL"
     polyA_signal     7260..7265
BASE COUNT     2601 a   1377 c   1509 g   2417 t
ORIGIN         Unreported.

Pph16.Gb_Vi  Length: 7904  September 16, 1994  09:00  Type: N  Check: 5970  ..

1  ACTACAATAA TTCATGTATA AAACTAAGGG CGTAACCGAA ATCGGTTGAA

51  CCGAAACCGG TTAGTATAAA AGCAGACATT TTATGCACCA AAAGAGAACT

101  GCAATGTTTC AGGACCCACA GGAGCGACCC AGAAAGTTAC CACAGTTATG

151  CACAGAGCTG CAAACAACTA TACATGATAT AATATTAGAA TGTGTGTACT

201  GCAAGCAACA GTTACTGCGA CGTGAGGTAT ATGACTTTGC TTTTCGGGAT

251  TTATGCATAG TATATAGAGA TGGGAATCCA TATGCTGTAT GTGATAAATG

301  TTTAAAGTTT TATTCTAAAA TTAGTGAGTA TAGACATTAT TGTTATAGTg

351  TGTATGGAAC AACATTAGAA CAGCAATACA ACAAACCGTT GTGTGATTTG

401  TTAATTAGGT GTATTAACTG TCAAAAGCCA CTGTGTCCTG AAGAAAAGCA

451  AAGACATCTG GACAAAAAGC AAAGATTCCA TAATATAAGG GGTCGGTGGA

501  CCGGTCGATG TATGTCTTGT TGCAGATCAT CAAGAACACG TAGAGAAACC

551  CAGCTGTAAT CATGCATGGA GATACACCTA CATTGCATGA ATATATGTTA

601  GATTTGCAAC CAGAGACAAC TGATCTCTAC TGTTATGAGC AATTAAATGA

651  CAGCTCAGAG GAGGAGGATG AAATAGATGG TCCAGCTGGA CAAGCAGAAC

701  CGGACAGAGC CCATTACAAT ATTGTAACCT TTTGTTGCAA GTGTGACTCT

751  ACGCTTCGGT TGTGCGTACA AAGCACACAC GTAGACATTC GTACTTTGGA

801  AGACCTGTTA ATGGGCACAC TAGGAATTGT GTGCCCCATC TGTTCTCAGA

851  AACCATAATC TACCATGGCT GATCCTGCAG GTACCAATGG GGAAGAGGGT

901  ACGGGATGTA ATGGATGGTT TTATGTAGAG GCTGTAGTGG AAAAAAAAAC
```

FIG. 3C

```
 951  AGGGGATGCT ATATCAGATG ACGAGAACGA AAATGACAGT GATACAGGTG
1001  AAGATTTGGT AGATTTTATA GTAAATGATA ATGATTATTT AACACAGGCA
1051  GAAACAGAGA CAGCACATGC GTTGTTTACT GCACAGGAAG CAAAACAACA
1101  TAGAGATGCA GTACAGGTTC TAAAACGAAA GTATTTGGTA GTCCACTTAG
1151  TGATATTAGT GGATGTGTAG ACAATAATAT TAGTCCTAGA TTAAAAGCTA
1201  TATGTATAGA AAAACAAAGT AGAGCTGCAA AAAGGAGATT ATTTGAAAGC
1251  GAAGACAGCG GGTATGGCAA TACTGAAGTG GAAACTCAGC AGATGTTACA
1301  GGTAGAAGGG CGCCATGAGA CTGAAACACC ATGTAGTCAG TATAGTGGTG
1351  GAAGTGGGGG TGGTTGCAGT CAGTACAGTA GTGGAAGTGG GGGAGAGGGT
1401  GTTAGTGAAA GACACACTAT ATGCCAAACA CCACTTACAA ATATTTTAAA
1451  TGTACTAAAA ACTAGTAATG CAAAGGCAGC AATGTTAGCA AAATTTAAAG
1501  AGTTATACGG GGTGAGTTTT TCAGAATTAG TAAGACCATT TAAAAGTAAT
1551  AAATCAACGT GTTGCGATTG GTGTATTGCT GCATTTGGAC TTACACCCAG
1601  TATAGCTGAC AGTATAAAAA CACTATTACA ACAATATTGT TTATATTTAC
1651  ACATTCAAAG TTTAGCATGT TCATGGGGAA TGGTTGTGTT ACTATTAGTA
1701  AGATATAAAT GTGGAAAAAA TAGAGAAACA ATTGAAAAAT TGCTGTCTAA
1751  ACTATTATGT GTGTCTCCAA TGTGTATGAT GATAGAGCCT CCAAAATTGC
1801  GTAGTACAGC AGCAGCATTA TATTGGTATA AACAGGTAT ATCAAATATT
1851  AGTGAAGTGT ATGGAGACAC GCCAGAATGG ATACAAAGAC AAACAGTATT
1901  ACAACATAGT TTTAATGATT GTACATTTGA ATTATCACAG ATGGTACAAT
1951  GGGCCTACGA TAATGACATA GTAGACGATA GTGAAATTGC ATATAAATAT
2001  GCACAATTGG CAGACACTAA TAGTAATGCA AGTGCCTTTC TAAAAAGTAA
2051  TTCACAGGCA AAAATTGTAA AGGATTGTGC AACAATGTGT AGACATTATA
2101  AACGAGCAGA AAAAAACAA ATGAGTATGA GTCAATGGAT AAAATATAGA
2151  TGTGATAGGG TAGATGATGG AGGTGATTGG AAGCAAATTG TTATGTTTTT
2201  AAGGTATCAA GGTGTAGAGT TTATGTCATT TTTAACTGCA TTAAAAAGAT
2251  TTTTGCAAGG CATACCTAAA AAAAATTGCA TATTACTATA TGGTGCAGCT
2301  AACACAGGTA AATCATTATT TGGTATGAGT TTAATGAAAT TTCTGCAAGG
2351  GTCTGTAATA TGTTTTGTAA ATTCTAAAAG CCATTTTTGG TTACAACCAT
2401  TAGCAGATGC CAAAATAGGT ATGTTAGATG ATGCTACAGT GCCCTGTTGG
```

FIG. 3D

```
2451  AACTACATAG ATGACAATTT AAGAAATGCA TTGGATGGAA ATTTAGTTTC
2501  TATGGATGTA AAGCATAGAC CATTGGTACA ACTAAAATGC CCTCCATTAT
2551  TAATTACATC TAACATTAAT GCTGGTACAG ATTCTAGGTG GCCTTATTTA
2601  CATAATAGAT TGGTGGTGTT TACATTTCCT AATGAGTTTC CATTTGACGA
2651  AAACGGAAAT CCAGTGTATG AGCTTAATGA TAAGAACTGG AAATCCTTTT
2701  TCTCAAGGAC GTGGTCCAGA TTAAGTTTGC ACGAGGACGA GGACAAGGAA
2751  AACGATGGAG ACTCTTTGCC AACGTTTAAA TGTGTGTCAG GACAAAATAC
2801  TAACACATTA TGAAAATGAT AGTACAGACC TACGTGACCA TATAGACTAT
2851  TGGAAACACA TGCGCCTAGA ATGTGCTATT TATTACAAGG CCAGAGAAAT
2901  GGGATTTAAA CATATTAACC ACCAAGTGGT GCCAACACTG GCTGTATCAA
2951  AGAATAAAGC ATTACAAGCA ATTGAACTGC AACTAACGTT AGAAACAATA
3001  TATAACTCAC AATATAGTAA TGAAAAGTGG ACATTACAAG ACGTTAGCCT
3051  TGAAGTGTAT TTAACTGCAC CAACAGGATG TATAAAAAAA CATGGATATA
3101  CAGTGGAAGT GCAGTTTGAT GGAGACATAT GCAATACAAT GCATTATACA
3151  AACTGGACAC ATATATATAT TTGTGAAGAA GCATCAGTAA CTGTGGTAGA
3201  GGGTCAAGTT GACTATTATG GTTTATATTA TGTTCATGAA GGAATACGAA
3251  CATATTTTGT GCAGTTTAAA GATGATGCAG AAAAATATAG TAAAAATAAA
3301  GTATGGGAAG TTCATGCGGG TGGTCAGGTA ATATTATGTC CTACATCTGT
3351  GTTTAGCAGC AACGAAGTAT CCTCTCCTGA AATTATTAGG CAGCACTTGG
3401  CCAACCACCC CGCCGCGACC CATACCAAAG CCGTCGCCTT GGGCACCGAA
3451  GAAACACAGA CGACTATCCA GCGACCAAGA TCAGAGCCAG ACACCGGAAA
3501  CCCCTGCCAC ACCACTAAGT TGTTGCACAG AGACTCAGTG GACAGTGCTC
3551  CAATCCTCAC TGCATTTAAC AGCTCACACA AAGGACGGAT TAACTGTAAT
3601  AGTAACACTA CACCCATAGT ACATTTAAAA GGTGATGCTA ATACTTTAAA
3651  ATGTTTAAGA TATAGATTTA AAAAGCATTG TACATTGTAT ACTGCAGTGT
3701  CGTCTACATG GCATTGGACA GGACATAATG TAAAACATAA AAGTGCAATT
3751  GTTACACTTA CATATGATAG TGAATGGCAA CGTGACCAAT TTTTGTCTCA
3801  AGTTAAAATA CCAAAAACTA TTACAGTGTC TACTGGATTT ATGTCTATAT
3851  GACAAATCTT GATACTGCAT CCACAACATT ACTGGCGTGC TTTTGCTTT
3901  GCTTTGTGTG CTTTTGTGTG TCTGCCTATT AATACGTCCG CTGCTTTTGT
```

FIG. 3E

```
3951  CTGTGTCTAC ATACACATCA TTAATAATAT TGGTATTACT ATTGTGGATA
4001  ACAGCAGCCT CTGCGTTTAG GTGTTTTATT GTATATATTA TATTTGTTTA
4051  TATACCATTA TTTTTAATAC ATACACATGC ACGCTTTTA  ATTACATAAT
4101  GTATATGTAC ATAATGTAAT TGTTACATAT AATTGTTGTA TACCATAACT
4151  TACTATTTTT TCTTTTTTAT TTTCATATAT AATTTTTTTT TTTGTTTGTT
4201  TGTTTGTTTT TTAATAAACT GTTATTACTT AACAATGCGA CACAAACGTT
4251  CTGCAAAACG CACAAAACGT GCATCGGCTA CCCAACTTTA TAAAACATGC
4301  AAACAGGCAG GTACATGTCC ACCTGACATT ATACCTAAGG TTGAAGGCAA
4351  AACTATTGCT GAACAAATAT TACAATATGG AAGTATGGGT GTATTTTTTG
4401  GTGGGTTAGG AATTGGAACA GGGTCGGGTA CAGGCGGACG CACTGGGTAT
4451  ATTCCATTGG GAACAAGGCC TCCCACAGCT ACAGATACAC TTGCTCCTGT
4501  AAGACCCCCT TTAACAGTAG ATCCTGTGGG CCCTTCTGAT CCTTCTATAG
4551  TTTCTTTAGT GGAAGAAACT AGTTTTATTG ATGCTGGTGC ACCAACATCT
4601  GTACCTTCCA TTCCCCCAGA TGTATCAGGA TTTAGTATTA CTACTTCAAC
4651  TGATACCACA CCTGCTATAT AGATATTAA  TAATACTGTT ACTACTGTTA
4701  CTACACATAA TAATCCCACT TTCACTGACC CATCTGTATT GCAGCCTCCA
4751  ACACCTGCAG AAACTGGAGG GCATTTACA  CTTTCATCAT CCACTATTAG
4801  TACACATAAT TATGAAGAAA TTCCTATGGA TACATTTATT GTTAGCACAA
4851  ACCCTAACAC AGTAACTAGT AGCACACCCA TACCAGGGTC TCGCCCAGTG
4901  GCACGCCTAG GATTATATAG TCGCACAACA CAACAGGTTA AAGTTGTAGA
4951  CCCTGCTTTT GTAACCACTC CCACTAAACT TATTACATAT GATAATCCTG
5001  CATATGAAGG TATAGATGTG GATAATACAT TATATTTTTC TAGTAATGAT
5051  AATAGTATTA ATATAGCTCC AGATCCTGAC TTTTTGGATA TAGTTGCTTT
5101  ACATAGGCCA GCATTAACCT CTAGGCGTAC TGGCATTAGG TACAGTAGAA
5151  TTGGTAATAA ACAAACACTA CGTACTCGTA GTGGAAAATC TATAGGTGCT
5201  AAGGTACATT ATTATTATGA TTTAAGTACT ATTGATCCTG CAGAAGAAAT
5251  AGAATTACAA ACTATAACAC CTTCTACATA TACTACCACT TCACATGCAG
5301  CCTCACCTAC TTCTATTAAT AATGGATTAT ATGATATTTA TGCAGATGAC
5351  TTTATTACAG ATACTTCTAC AACCCCGGTA CCATCTGTAC CCTCTACATC
5401  TTTATCAGGT TATATTCCTG CAAATACAAC AATTCCTTTT GGTGGTGCAT
```

FIG. 3F

```
5451  ACAATATTCC TTTAGTATCA GGTCCTGATA TACCCATTAA TATAACTGAC
5501  CAAGCTCCTT CATTAATTCC TATAGTTCCA GGGTCTCCAC AATATACAAT
5551  TATTGCTGAT GCAGGTGACT TTTATTTACA TCCTAGTTAT TACATGTTAC
5601  GAAAACGACG TAAACGTTTA CCATATTTTT TTTCAGATGT CTCTTTGGCT
5651  GCCTAGTGAG GCCACTGTCT ACTTGCCTCC TGTCCCAGTA TCTAAGGTTG
5701  TAAGCACGGA TGAATATGTT GCACGCACAA ACATATATTA TCATGCAGGA
5751  ACATCCAGAC TACTTGCAGT TGGACATCCC TATTTTCCTA TTAAAAAACC
5801  TAACAATAAC AAAATATTAG TTCCTAAAGT ATCAGGATTA CAATACAGGG
5851  TATTTAGAAT ACATTTACCT GACCCCAATA AGTTTGGTTT TCCTGACACC
5901  TCATTTTATA ATCCAGATAC ACAGCGGCTG GTTTGGGCCT GTGTAGGTGT
5951  TGAGGTAGGT CGTGGTCAGC CATTAGGTGT GGGCATTAGT GGCCATCCTT
6001  TATTAAATAA ATTGGATGAC ACAGAAAATG CTAGTGCTTA TGCAGCAAAT
6051  GCAGGTGTGG ATAATAGAGA ATGTATATCT ATGGATTACA AACAAACACA
6101  ATTGTGTTTA ATTGGTTGCA AACCACCTAT AGGGGAACAC TGGGGCAAAG
6151  GATCCCCATG TACCAATGTT GCAGTAAATC CAGGTGATTG TCCACCATTA
6201  GAGTTAATAA ACACAGTTAT TCAGGATGGT GATATGGTTC ATACTGGCTT
6251  TGGTGCTATG GACTTTACTA CATTACAGGC TAACAAAAGT GAAGTTCCAC
6301  TGGATATTTG TACATCTATT TGCAAATATC CAGATTATAT TAAAATGGTG
6351  TCAGAACCAT ATGGCGACAG CTTATTTTTT TATTTACGAA GGGAACAAAT
6401  GTTTGTTAGA CATTTATTTA ATAGGGCTGG TACTGTTGGT GAAAATGTAC
6451  CAGACGATTT ATACATTAAA GGCTCTGGGT CTACTGCAAA TTTAGCCAGT
6501  TCAAATTATT TTCCTACACC TAGTGGTTCT ATGGTTACCT CTGATGCCCA
6551  AATATTCAAT AAACCTTATT GGTTACAACG AGCACAGGGC CACAATAATG
6601  GCATTTGTTG GGGTAACCAA CTATTTGTTA CTGTTGTTGA TACTACACGC
6651  AGTACAAATA TGTCATTATG TGCTGCCATA TCTACTTCAG AAACTACATA
6701  TAAAAATACT AACTTTAAGG AGTACCTACG ACATGGGGAG GAATATGATT
6751  TACAGTTTAT TTTTCAACTG TGCAAAATAA CCTTAACTGC AGACGTTATG
6801  ACATACATAC ATTCTATGAA TTCCACTATT TTGGAGGACT GGAATTTTGG
6851  TCTACAACCT CCCCCAGGAG GCACACTAGA AGATACTTAT AGGTTTGTAA
6901  CCCAGGCAAT TGCTTGTCAA AAACATACAC CTCCAGCACC TAAAGAAGAT
```

FIG. 3G

6951 GATCCCCTTA AAAAATACAC TTTTTGGGAA GTAAATTTAA AGGAAAAGTT
7001 TTCTGCAGAC CTAGATCAGT TTCCTTTAGG ACGCAAATTT TTACTACAAG
7051 CAGGATTGAA GGCCAAACCA AAATTTACAT TAGGAAAACG AAAAGCTACA
7101 CCCACCACCT CATCTACCTC TACAACTGCT AAACGCAAAA AACGTAAGCT
7151 GTAAGTATTG TATGTATGTT GAATTAGTGT TGTTTGTTGT GTATATGTTT
7201 GTATGTGCTT GTATGTGCTT GTAAATATTA AGTTGTATGT GTGTTTGTAT
7251 GTATGGTATA ATAAACACGT GTGTATGTGT TTTTAAATGC TTGTGTAACT
7301 ATTGTGTCAT GCAACATAAA TAAACTTATT GTTTCAACAC CTACTAATTG
7351 TGTTGTGGTT ATTCATTGTA TATAAACTAT ATTTGCTACA TCCTGTTTTT
7401 GTTTTATATA TACTATATTT TGTAGCGCCA GGCCCATTTT GTAGCTTCAA
7451 CCGAATTCGG TTGCATGCTT TTTGGCACAA AATGTGTTTT TTTAAATAGT
7501 TCTATGTCAG CAACTATGGT TTAAACTTGT ACGTTTCCTG CTTGCCATGC
7551 GTGCCAAATC CCTGTTTTCC TGACCTGCAC TGCTTGCCAA CCATTCCATT
7601 GTTTTTTACA CTGCACTATG TGCAACTACT GAATCACTAT GTACATTGTG
7651 TCATATAAAA TAAATCACTA TGCGCCAACG CCTTACATAC CGCTGTTAGG
7701 CACATATTTT TGGCTTGTTT TAACTAACCT AATTGCATAT TTGGCATAAG
7751 GTTTAAACTT CTAAGGCCAA CTAAATGTCA CCCTAGTTCA TACATGAACT
7801 GTGTAAAGGT TAGTCATACA TTGTTCATTT GTAAAACTGC ACATGGGTGT
7851 GTGCAAACCG ATTTTGGGTT ACACATTTAC AAGCAACTTA TATAATAATA
7901 CTAA

FIG. 3H

TRANSLATE of: pph16.gb_vi check: 6074 from: 83 to: 568
generated symbols 1 to 162.

LOCUS       PPH16     7904 bp DS-DNA circular VRL   18-MAR-1994
DEFINITION  Human papillomavirus type 16 (HPV16), complete
            genome.
ACCESSION   K02718
KEYWORDS    circular; complete genome
SOURCE      Papilloma virus type 16 DNA, isolated from a human
            invasive cervical carcinoma. . . .

Pph16.pep Length: 162 September 16, 1994 08:35
Type: P  Check: 2380  ..

1  MHQKRTAMFQ DPQERPRKLP QLCTELQTTI HDIILECVYC KQQLLRREVY

51  DFAFRDLCIV YRDGNPYAVC DKCLKFYSKI SEYRHYCYSL YGTTLEQQYN

101  KPLCDLLIRC INCQKPLCPE EKQRHLDKKQ RFHNIRGRWT GRCMSCCRSS

151  RTRRETQL*S CM

Start at position number 8.

Amino acid reference number 83 from start.

FIG. 4

TRANSLATE of: pph16.gb_vi check: 5970 from: 83 to: 568
generated symbols 1 to 162.

LOCUS       PPH16    7904 bp DS-DNA circular VRL    18-MAR-1994
DEFINITION  Human papillomavirus type 16 (HPV16), complete
            genome
ACCESSION   K02718
KEYWORDS    circular; complete genome
SOURCE      Papilloma virus type 16 DNA, isolated from a human
            invasive cervical carcinoma. . . .

Pph16.pep Length: 162 September 16, 1994 09:01
Type: P  Check: 2710  ..

1  MHQKRTAMFQ DPQERPRKLP QLCTELQTTI HDIILECVYC KQQLLRREVY

51  DFAFRDLCIV YRDGNPYAVC DKCLKFYSKI SEYRHYCYSV YGTTLEQQYN

101  KPLCDLLIRC INCQKPLCPE EKQRHLDKKQ RFHNIRGRWT GRCMSCCRSS

151  RTRRETQL*S CM

Start at position number 8.

Amino acid variant number 83 from start.

FIG. 5

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 7904 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( x i ) SEQUENCE DESCRIPTION: SEQ ID NO:1:

```
ACTACAATAA  TTCATGTATA  AAACTAAGGG  CGTAACCGAA  ATCGGTTGAA  CCGAAACCGG    60
TTAGTATAAA  AGCAGACATT  TTATGCACCA  AAAGAGAACT  GCAATGTTTC  AGGACCCACA   120
GGAGCGACCC  AGAAAGTTAC  CACAGTTATG  CACAGAGCTG  CAAACAACTA  TACATGATAT   180
AATATTAGAA  TGTGTGTACT  GCAAGCAACA  GTTACTGCGA  CGTGAGGTAT  ATGACTTTGC   240
TTTTCGGGAT  TTATGCATAG  TATATAGAGA  TGGGAATCCA  TATGCTGTAT  GTGATAAATG   300
TTTAAAGTTT  TATTCTAAAA  TTAGTGAGTA  TAGACATTAT  TGTTATAGTT  TGTATGGAAC   360
AACATTAGAA  CAGCAATACA  ACAAACCGTT  GTGTGATTTG  TTAATTAGGT  GTATTAACTG   420
TCAAAAGCCA  CTGTGTCCTG  AAGAAAAGCA  AGACATCTG   GACAAAAGC   AAAGATTCCA   480
TAATATAAGG  GGTCGGTGGA  CCGGTCGATG  TATGTCTTGT  TGCAGATCAT  CAAGAACACG   540
TAGAGAAACC  CAGCTGTAAT  CATGCATGGA  GATACACCTA  CATTGCATGA  ATATATGTTA   600
GATTTGCAAC  CAGAGACAAC  TGATCTCTAC  TGTTATGAGC  AATTAAATGA  CAGCTCAGAG   660
GAGGAGGATG  AAATAGATGG  TCCAGCTGGA  CAAGCAGAAC  CGGACAGAGC  CCATTACAAT   720
ATTGTAACCT  TTTGTTGCAA  GTGTGACTCT  ACGCTTCGGT  TGTGCGTACA  AAGCACACAC   780
GTAGACATTC  GTACTTTGGA  AGACCTGTTA  ATGGGCACAC  TAGGAATTGT  GTGCCCCATC   840
TGTTCTCAGA  AACCATAATC  TACCATGGCT  GATCCTGCAG  GTACCAATGG  GGAAGAGGGT   900
ACGGGATGTA  ATGGATGGTT  TTATGTAGAG  GCTGTAGTGG  AAAAAAAAAC  AGGGGATGCT   960
ATATCAGATG  ACGAGAACGA  AAATGACAGT  GATACAGGTG  AAGATTTGGT  AGATTTTATA  1020
GTAAATGATA  ATGATTATTT  AACACAGGCA  GAAACAGAGA  CAGCACATGC  GTTGTTTACT  1080
GCACAGGAAG  CAAAACAACA  TAGAGATGCA  GTACAGGTTC  TAAAACGAAA  GTATTTGGTA  1140
GTCCACTTAG  TGATATTAGT  GGATGTGTAG  ACAATAATAT  TAGTCCTAGA  TTAAAAGCTA  1200
TATGTATAGA  AAAACAAAGT  AGAGCTGCAA  AAAGGAGATT  ATTTGAAAGC  GAAGACAGCG  1260
GGTATGGCAA  TACTGAAGTG  GAAACTCAGC  AGATGTTACA  GGTAGAAGGG  CGCCATGAGA  1320
CTGAAACACC  ATGTAGTCAG  TATAGTGGTG  GAAGTGGGGG  TGGTTGCAGT  CAGTACAGTA  1380
```

| | | | | | | |
|---|---|---|---|---|---|---|
| GTGGAAGTGG | GGGAGAGGGT | GTTAGTGAAA | GACACACTAT | ATGCCAAACA | CCACTTACAA | 1440 |
| ATATTTAAA | TGTACTAAAA | ACTAGTAATG | CAAAGGCAGC | AATGTTAGCA | AAATTTAAAG | 1500 |
| AGTTATACGG | GGTGAGTTTT | TCAGAATTAG | TAAGACCATT | TAAAAGTAAT | AAATCAACGT | 1560 |
| GTTGCGATTG | GTGTATTGCT | GCATTTGGAC | TTACACCCAG | TATAGCTGAC | AGTATAAAAA | 1620 |
| CACTATTACA | ACAATATTGT | TTATATTTAC | ACATTCAAAG | TTAGCATGT | TCATGGGGAA | 1680 |
| TGGTTGTGTT | ACTATTAGTA | AGATATAAAT | GTGGAAAAAA | TAGAGAAACA | ATTGAAAAAT | 1740 |
| TGCTGTCTAA | ACTATTATGT | GTGTCTCCAA | TGTGTATGAT | GATAGAGCCT | CCAAAATTGC | 1800 |
| GTAGTACAGC | AGCAGCATTA | TATTGGTATA | AAACAGGTAT | ATCAAATATT | AGTGAAGTGT | 1860 |
| ATGGAGACAC | GCCAGAATGG | ATACAAAGAC | AAACAGTATT | ACAACATAGT | TTAATGATT | 1920 |
| GTACATTTGA | ATTATCACAG | ATGGTACAAT | GGGCCTACGA | TAATGACATA | GTAGACGATA | 1980 |
| GTGAAATTGC | ATATAAATAT | GCACAATTGG | CAGACACTAA | TAGTAATGCA | AGTGCCTTTC | 2040 |
| TAAAAGTAA | TTCACAGGCA | AAAATTGTAA | AGGATTGTGC | AACAATGTGT | AGACATTATA | 2100 |
| AACGAGCAGA | AAAAAAACAA | ATGAGTATGA | GTCAATGGAT | AAAATATAGA | TGTGATAGGG | 2160 |
| TAGATGATGG | AGGTGATTGG | AAGCAAATTG | TTATGTTTTT | AAGGTATCAA | GGTGTAGAGT | 2220 |
| TTATGTCATT | TTTAACTGCA | TTAAAAGAT | TTTGCAAGG | CATACCTAAA | AAAAATTGCA | 2280 |
| TATTACTATA | TGGTGCAGCT | AACACAGGTA | AATCATTATT | TGGTATGAGT | TTAATGAAAT | 2340 |
| TTCTGCAAGG | GTCTGTAATA | TGTTTTGTAA | ATTCTAAAAG | CCATTTTGG | TTACAACCAT | 2400 |
| TAGCAGATGC | CAAAATAGGT | ATGTTAGATG | ATGCTACAGT | GCCCTGTTGG | AACTACATAG | 2460 |
| ATGACAATTT | AAGAAATGCA | TTGGATGGAA | ATTTAGTTTC | TATGGATGTA | AAGCATAGAC | 2520 |
| CATTGGTACA | ACTAAAATGC | CCTCCATTAT | TAATTACATC | TAACATTAAT | GCTGGTACAG | 2580 |
| ATTCTAGGTG | GCCTTATTTA | CATAATAGAT | TGGTGGTGTT | TACATTTCCT | AATGAGTTTC | 2640 |
| CATTTGACGA | AAACGGAAAT | CCAGTGTATG | AGCTTAATGA | TAAGAACTGG | AAATCCTTTT | 2700 |
| TCTCAAGGAC | GTGGTCCAGA | TTAAGTTTGC | ACGAGGACGA | GGACAAGGAA | AACGATGGAG | 2760 |
| ACTCTTTGCC | AACGTTTAAA | TGTGTGTCAG | GACAAAATAC | TAACACATTA | TGAAAATGAT | 2820 |
| AGTACAGACC | TACGTGACCA | TATAGACTAT | TGGAAACACA | TGCGCCTAGA | ATGTGCTATT | 2880 |
| TATTACAAGG | CCAGAGAAAT | GGGATTTAAA | CATATTAACC | ACCAAGTGGT | GCCAACACTG | 2940 |
| GCTGTATCAA | AGAATAAAGC | ATTACAAGCA | ATTGAACTGC | AACTAACGTT | AGAAACAATA | 3000 |
| TATAACTCAC | AATATAGTAA | TGAAAGTGG | ACATTACAAG | ACGTTAGCCT | TGAAGTGTAT | 3060 |
| TTAACTGCAC | CAACAGGATG | TATAAAAAAA | CATGGATATA | CAGTGGAAGT | GCAGTTTGAT | 3120 |
| GGAGACATAT | GCAATACAAT | GCATTATACA | AACTGGACAC | ATATATATAT | TTGTGAAGAA | 3180 |
| GCATCAGTAA | CTGTGGTAGA | GGGTCAAGTT | GACTATTATG | GTTTATATTA | TGTTCATGAA | 3240 |
| GGAATACGAA | CATATTTTGT | GCAGTTTAAA | GATGATGCAG | AAAAATATAG | TAAAAATAAA | 3300 |
| GTATGGGAAG | TTCATGCGGG | TGGTCAGGTA | ATATTATGTC | CTACATCTGT | GTTTAGCAGC | 3360 |
| AACGAAGTAT | CCTCTCCTGA | AATTATTAGG | CAGCACTTGG | CCAACCACCC | CGCCGCGACC | 3420 |
| CATACCAAAG | CCGTCGCCTT | GGGCACCGAA | GAAACACAGA | CGACTATCCA | GCGACCAAGA | 3480 |
| TCAGAGCCAG | ACACCGGAAA | CCCCTGCCAC | ACCACTAAGT | TGTTGCACAG | AGACTCAGTG | 3540 |
| GACAGTGCTC | CAATCCTCAC | TGCATTTAAC | AGCTCACACA | AAGGACGGAT | TAACTGTAAT | 3600 |
| AGTAACACTA | CACCCATAGT | ACATTTAAAA | GGTGATGCTA | ATACTTTAAA | ATGTTAAGA | 3660 |
| TATAGATTTA | AAAAGCATTG | TACATTGTAT | ACTGCAGTGT | CGTCTACATG | GCATTGGACA | 3720 |
| GGACATAATG | TAAAACATAA | AAGTGCAATT | GTTACACTTA | CATATGATAG | TGAATGGCAA | 3780 |

```
CGTGACCAAT TTTTGTCTCA AGTTAAAATA CCAAAAACTA TTACAGTGTC TACTGGATTT  3840
ATGTCTATAT GACAAATCTT GATACTGCAT CCACAACATT ACTGGCGTGC TTTTTGCTTT  3900
GCTTTGTGTG CTTTTGTGTG TCTGCCTATT AATACGTCCG CTGCTTTTGT CTGTGTCTAC  3960
ATACACATCA TTAATAATAT TGGTATTACT ATTGTGGATA ACAGCAGCCT CTGCGTTTAG  4020
GTGTTTTATT GTATATATTA TATTTGTTTA TATACCATTA TTTTAATAC ATACACATGC   4080
ACGCTTTTTA ATTCATAAT GTATATGTAC ATAATGTAAT TGTTACATAT AATTGTTGTA   4140
TACCATAACT TACTATTTTT TCTTTTTTAT TTCATATAT AATTTTTTTT TTGTTTGTT    4200
TGTTTGTTTT TTAATAAACT GTTATTACTT AACAATGCGA CACAAACGTT CTGCAAAACG  4260
CACAAAACGT GCATCGGCTA CCCAACTTTA TAAAACATGC AAACAGGCAG GTACATGTCC  4320
ACCTGACATT ATACCTAAGG TTGAAGGCAA AACTATTGCT GAACAAATAT TACAATATGG  4380
AAGTATGGGT GTATTTTTG GTGGGTTAGG AATTGGAACA GGGTCGGGTA CAGGCGGACG   4440
CACTGGGTAT ATTCCATTGG GAACAAGGCC TCCCACAGCT ACAGATACAC TTGCTCCTGT  4500
AAGACCCCCT TTAACAGTAG ATCCTGTGGG CCCTTCTGAT CCTTCTATAG TTTCTTTAGT  4560
GGAAGAAACT AGTTTTATTG ATGCTGGTGC ACCAACATCT GTACCTTCCA TTCCCCAGA   4620
TGTATCAGGA TTTAGTATTA CTACTTCAAC TGATACCACA CCTGCTATAT AGATATTAA   4680
TAATACTGTT ACTACTGTTA CTACACATAA TAATCCCACT TTCACTGACC CATCTGTATT  4740
GCAGCCTCCA ACACCTGCAG AAACTGGAGG GCATTTTACA CTTTCATCAT CCACTATTAG  4800
TACACATAAT TATGAAGAAA TTCCTATGGA TACATTTATT GTTAGCACAA ACCCTAACAC  4860
AGTAACTAGT AGCACACCCA TACCAGGGTC TCGCCCAGTG GCACGCCTAG GATTATATAG  4920
TCGCACAACA CAACAGGTTA AGTTGTAGA CCCTGCTTTT GTAACCACTC CCACTAAACT   4980
TATTACATAT GATAATCCTG CATATGAAGG TATAGATGTG GATAATACAT TATATTTTC   5040
TAGTAATGAT AATAGTATTA ATATAGCTCC AGATCCTGAC TTTTTGGATA TAGTTGCTTT  5100
ACATAGGCCA GCATTAACCT CTAGGCGTAC TGGCATTAGG TACAGTAGAA TTGGTAATAA  5160
ACAAACACTA CGTACTCGTA GTGGAAAATC TATAGGTGCT AAGGTACATT ATTATTATGA  5220
TTAAGTACT ATTGATCCTG CAGAAGAAAT AGAATTACAA ACTATAACAC CTTCTACATA    5280
TACTACCACT TCACATGCAG CCTCACCTAC TTCTATTAAT AATGGATTAT ATGATATTTA  5340
TGCAGATGAC TTTATTACAG ATACTTCTAC AACCCCGGTA CCATCTGTAC CCTCTACATC  5400
TTTATCAGGT TATATTCCTG CAAATACAAC AATTCCTTTT GGTGGTGCAT ACAATATTCC  5460
TTAGTATCA GGTCCTGATA TACCCATTAA TAATAACTGAC CAAGCTCCTT CATTAATTCC  5520
TATAGTTCCA GGGTCTCCAC AATATACAAT TATTGCTGAT GCAGGTGACT TTATTTACA   5580
TCCTAGTTAT TACATGTTAC GAAAACGACG TAAACGTTTA CCATATTTTT TTCAGATGT   5640
CTCTTTGGCT GCCTAGTGAG GCCACTGTCT ACTTGCCTCC TGTCCCAGTA TCTAAGGTTG  5700
TAAGCACGGA TGAATATGTT GCACGCACAA ACATATATTA TCATGCAGGA ACATCCAGAC  5760
TACTTGCAGT TGGACATCCC TATTTTCCTA TTAAAAAACC TAACAATAAC AAAATATTAG  5820
TTCCTAAAGT ATCAGGATTA CAATACAGGG TATTTAGAAT ACATTACCT GACCCCAATA   5880
AGTTTGGTTT TCCTGACACC TCATTTTATA ATCCAGATAC ACAGCGGCTG GTTTGGGCCT  5940
GTGTAGGTGT TGAGGTAGGT CGTGGTCAGC CATTAGGTGT GGGCATTAGT GGCCATCCTT  6000
TATTAAATAA ATTGGATGAC ACAGAAAATG CTAGTGCTTA TGCAGCAAAT GCAGGTGTGG  6060
ATAATAGAGA ATGTATATCT ATGGATTACA AACAAACACA ATTGTGTTTA ATTGGTTGCA  6120
AACCACCTAT AGGGGAACAC TGGGGCAAAG GATCCCCATG TACCAATGTT GCAGTAAATC  6180
```

| | | | | | |
|---|---|---|---|---|---|
| CAGGTGATTG | TCCACCATTA | GAGTTAATAA | ACACAGTTAT | TCAGGATGGT | GATATGGTTC | 6240
| ATACTGGCTT | TGGTGCTATG | GACTTACTA | CATTACAGGC | TAACAAAAGT | GAAGTTCCAC | 6300
| TGGATATTTG | TACATCTATT | TGCAAATATC | CAGATTATAT | TAAAATGGTG | TCAGAACCAT | 6360
| ATGGCGACAG | CTTATTTTTT | TATTTACGAA | GGGAACAAAT | GTTGTTAGA | CATTTATTTA | 6420
| ATAGGGCTGG | TACTGTTGGT | GAAAATGTAC | CAGACGATTT | ATACATTAAA | GGCTCTGGGT | 6480
| CTACTGCAAA | TTTAGCCAGT | TCAAATTATT | TTCCTACACC | TAGTGGTTCT | ATGGTTACCT | 6540
| CTGATGCCCA | AATATTCAAT | AAACCTTATT | GGTTACAACG | AGCACAGGGC | CACAATAATG | 6600
| GCATTTGTTG | GGGTAACCAA | CTATTTGTTA | CTGTTGTTGA | TACTACACGC | AGTACAAATA | 6660
| TGTCATTATG | TGCTGCCATA | TCTACTTCAG | AAACTACATA | TAAAAATACT | AACTTTAAGG | 6720
| AGTACCTACG | ACATGGGGAG | GAATATGATT | TACAGTTTAT | TTTTCAACTG | TGCAAAATAA | 6780
| CCTTAACTGC | AGACGTTATG | ACATACATAC | ATTCTATGAA | TTCCACTATT | TTGGAGGACT | 6840
| GGAATTTTGG | TCTACAACCT | CCCCCAGGAG | GCACACTAGA | AGATACTTAT | AGGTTTGTAA | 6900
| CCCAGGCAAT | TGCTTGTCAA | AAACATACAC | CTCCAGCACC | TAAAGAAGAT | GATCCCCTTA | 6960
| AAAAATACAC | TTTTTGGGAA | GTAAATTTAA | AGGAAAAGTT | TTCTGCAGAC | CTAGATCAGT | 7020
| TTCCTTTAGG | ACGCAAATTT | TTACTACAAG | CAGGATTGAA | GGCCAAACCA | AAATTTACAT | 7080
| TAGGAAAACG | AAAAGCTACA | CCCACCACCT | CATCTACCTC | TACAACTGCT | AAACGCAAAA | 7140
| AACGTAAGCT | GTAAGTATTG | TATGTATGTT | GAATTAGTGT | TGTTTGTTGT | GTATATGTTT | 7200
| GTATGTGCTT | GTATGTGCTT | GTAAATATTA | AGTTGTATGT | GTGTTTGTAT | GTATGGTATA | 7260
| ATAAACACGT | GTGTATGTGT | TTTTAAATGC | TTGTGTAACT | ATTGTGTCAT | GCAACATAAA | 7320
| TAAACTTATT | GTTCAACAC | CTACTAATTG | TGTTGTGGTT | ATTCATTGTA | TATAAACTAT | 7380
| ATTTGCTACA | TCCTGTTTTT | GTTTTATATA | TACTATATTT | TGTAGCGCCA | GGCCCATTTT | 7440
| GTAGCTTCAA | CCGAATTCGG | TTGCATGCTT | TTTGGCACAA | AATGTGTTTT | TTTAAATAGT | 7500
| TCTATGTCAG | CAACTATGGT | TTAAACTTGT | ACGTTCCTG | CTTGCCATGC | GTGCCAAATC | 7560
| CCTGTTTTCC | TGACCTGCAC | TGCTTGCCAA | CCATTCCATT | GTTTTTACA | CTGCACTATG | 7620
| TGCAACTACT | GAATCACTAT | GTACATTGTG | TCATATAAAA | TAAATCACTA | TGCGCCAACG | 7680
| CCTTACATAC | CGCTGTTAGG | CACATATTTT | TGGCTTGTTT | TAACTAACCT | AATTGCATAT | 7740
| TTGGCATAAG | GTTTAAACTT | CTAAGGCCAA | CTAAATGTCA | CCCTAGTTCA | TACATGAACT | 7800
| GTGTAAAGGT | TAGTCATACA | TTGTTCATTT | GTAAAACTGC | ACATGGGTGT | GTGCAAACCG | 7860
| ATTTGGGTT | ACACATTTAC | AAGCAACTTA | TATAATAATA | CTAA | | 7904

( 2 ) INFORMATION FOR SEQ ID NO:2:

( i ) SEQUENCE CHARACTERISTICS:
  ( A ) LENGTH: 7904 base pairs
  ( B ) TYPE: nucleic acid
  ( C ) STRANDEDNESS: double
  ( D ) TOPOLOGY: circular ( i i ) MOLECULE TYPE: DNA (genomic)

( i i i ) HYPOTHETICAL: NO ( x i ) SEQUENCE DESCRIPTION: SEQ ID NO:2:

| | | | | | |
|---|---|---|---|---|---|
| ACTACAATAA | TTCATGTATA | AAACTAAGGG | CGTAACCGAA | ATCGGTTGAA | CCGAAACCGG | 60
| TTAGTATAAA | AGCAGACATT | TTATGCACCA | AAAGAGAACT | GCAATGTTTC | AGGACCCACA | 120
| GGAGCGACCC | AGAAAGTTAC | CACAGTTATG | CACAGAGCTG | CAAACAACTA | TACATGATAT | 180
| AATATTAGAA | TGTGTGTACT | GCAAGCAACA | GTTACTGCGA | CGTGAGGTAT | ATGACTTTGC | 240

-continued

| | | | | | | |
|---|---|---|---|---|---|---|
| TTTTCGGGAT | TTATGCATAG | TATATAGAGA | TGGGAATCCA | TATGCTGTAT | GTGATAAATG | 300 |
| TTTAAAGTTT | TATTCTAAAA | TTAGTGAGTA | TAGACATTAT | TGTTATAGTG | TGTATGGAAC | 360 |
| AACATTAGAA | CAGCAATACA | ACAAACCGTT | GTGTGATTTG | TTAATTAGGT | GTATTAACTG | 420 |
| TCAAAAGCCA | CTGTGTCCTG | AAGAAAAGCA | AAGACATCTG | GACAAAAAGC | AAAGATTCCA | 480 |
| TAATATAAGG | GGTCGGTGGA | CCGGTCGATG | TATGTCTTGT | TGCAGATCAT | CAAGAACACG | 540 |
| TAGAGAAACC | CAGCTGTAAT | CATGCATGGA | GATACACCTA | CATTGCATGA | ATATATGTTA | 600 |
| GATTTGCAAC | CAGAGACAAC | TGATCTCTAC | TGTTATGAGC | AATTAAATGA | CAGCTCAGAG | 660 |
| GAGGAGGATG | AAATAGATGG | TCCAGCTGGA | CAAGCAGAAC | CGGACAGAGC | CCATTACAAT | 720 |
| ATTGTAACCT | TTTGTTGCAA | GTGTGACTCT | ACGCTTCGGT | TGTGCGTACA | AAGCACACAC | 780 |
| GTAGACATTC | GTACTTTGGA | AGACCTGTTA | ATGGGCACAC | TAGGAATTGT | GTGCCCCATC | 840 |
| TGTTCTCAGA | AACCATAATC | TACCATGGCT | GATCCTGCAG | GTACCAATGG | GGAAGAGGGT | 900 |
| ACGGGATGTA | ATGGATGGTT | TTATGTAGAG | GCTGTAGTGG | AAAAAAAAC | AGGGGATGCT | 960 |
| ATATCAGATG | ACGAGAACGA | AAATGACAGT | GATACAGGTG | AAGATTTGGT | AGATTTTATA | 1020 |
| GTAAATGATA | ATGATTATTT | AACACAGGCA | GAAACAGAGA | CAGCACATGC | GTTGTTTACT | 1080 |
| GCACAGGAAG | CAAAACAACA | TAGAGATGCA | GTACAGGTTC | TAAAACGAAA | GTATTTGGTA | 1140 |
| GTCCACTTAG | TGATATTAGT | GGATGTGTAG | ACAATAATAT | TAGTCCTAGA | TTAAAAGCTA | 1200 |
| TATGTATAGA | AAAACAAAGT | AGAGCTGCAA | AAGGAGATT | ATTTGAAAGC | GAAGACAGCG | 1260 |
| GGTATGGCAA | TACTGAAGTG | GAAACTCAGC | AGATGTTACA | GGTAGAAGGG | CGCCATGAGA | 1320 |
| CTGAAACACC | ATGTAGTCAG | TATAGTGGTG | GAAGTGGGGG | TGGTTGCAGT | CAGTACAGTA | 1380 |
| GTGGAAGTGG | GGGAGAGGGT | GTTAGTGAAA | GACACACTAT | ATGCCAAACA | CCACTTACAA | 1440 |
| ATATTTTAAA | TGTACTAAAA | ACTAGTAATG | CAAAGGCAGC | AATGTTAGCA | AAATTTAAAG | 1500 |
| AGTTATACGG | GGTGAGTTTT | TCAGAATTAG | TAAGACCATT | TAAAAGTAAT | AAATCAACGT | 1560 |
| GTTGCGATTG | GTGTATTGCT | GCATTTGGAC | TTACACCCAG | TATAGCTGAC | AGTATAAAAA | 1620 |
| CACTATTACA | ACAATATTGT | TTATATTTAC | ACATTCAAAG | TTTAGCATGT | TCATGGGGAA | 1680 |
| TGGTTGTGTT | ACTATTAGTA | AGATATAAAT | GTGGAAAAAA | TAGAGAAACA | ATTGAAAAT | 1740 |
| TGCTGTCTAA | ACTATTATGT | GTGTCTCCAA | TGTGTATGAT | GATAGAGCCT | CCAAAATTGC | 1800 |
| GTAGTACAGC | AGCAGCATTA | TATTGGTATA | AACAGGTAT | ATCAAATATT | AGTGAAGTGT | 1860 |
| ATGGAGACAC | GCCAGAATGG | ATACAAAGAC | AAACAGTATT | ACAACATAGT | TTAATGATT | 1920 |
| GTACATTTGA | ATTATCACAG | ATGGTACAAT | GGGCCTACGA | TAATGACATA | GTAGACGATA | 1980 |
| GTGAAATTGC | ATATAAATAT | GCACAATTGG | CAGACACTAA | TAGTAATGCA | AGTGCCTTTC | 2040 |
| TAAAAAGTAA | TTCACAGGCA | AAAATTGTAA | AGGATTGTGC | AACAATGTGT | AGACATTATA | 2100 |
| AACGAGCAGA | AAAAAACAA | ATGAGTATGA | GTCAATGGAT | AAAATATAGA | TGTGATAGGG | 2160 |
| TAGATGATGG | AGGTGATTGG | AAGCAAATTG | TTATGTTTTT | AAGGTATCAA | GGTGTAGAGT | 2220 |
| TTATGTCATT | TTTAACTGCA | TTAAAAGAT | TTTGCAAGG | CATACCTAAA | AAAAATTGCA | 2280 |
| TATTACTATA | TGGTGCAGCT | AACACAGGTA | AATCATTATT | TGGTATGAGT | TTAATGAAAT | 2340 |
| TTCTGCAAGG | GTCTGTAATA | TGTTTTGTAA | ATTCTAAAAG | CCATTTTTGG | TTACAACCAT | 2400 |
| TAGCAGATGC | CAAAATAGGT | ATGTTAGATG | ATGCTACAGT | GCCCTGTTGG | AACTACATAG | 2460 |
| ATGACAATTT | AAGAAATGCA | TTGGATGGAA | ATTTAGTTTC | TATGGATGTA | AAGCATAGAC | 2520 |
| CATTGGTACA | ACTAAAATGC | CCTCCATTAT | TAATTACATC | TAACATTAAT | GCTGGTACAG | 2580 |
| ATTCTAGGTG | GCCTTATTTA | CATAATAGAT | TGGTGGTGTT | TACATTTCCT | AATGAGTTTC | 2640 |

| | | | | | |
|---|---|---|---|---|---|
| CATTTGACGA | AAACGGAAAT | CCAGTGTATG | AGCTTAATGA | TAAGAACTGG | AAATCCTTTT | 2700 |
| TCTCAAGGAC | GTGGTCCAGA | TTAAGTTTGC | ACGAGGACGA | GGACAAGGAA | AACGATGGAG | 2760 |
| ACTCTTTGCC | AACGTTTAAA | TGTGTGTCAG | GACAAAATAC | TAACACATTA | TGAAAATGAT | 2820 |
| AGTACAGACC | TACGTGACCA | TATAGACTAT | TGGAAACACA | TGCGCCTAGA | ATGTGCTATT | 2880 |
| TATTACAAGG | CCAGAGAAAT | GGGATTTAAA | CATATTAACC | ACCAAGTGGT | GCCAACACTG | 2940 |
| GCTGTATCAA | AGAATAAAGC | ATTACAAGCA | ATTGAACTGC | AACTAACGTT | AGAAACAATA | 3000 |
| TATAACTCAC | AATATAGTAA | TGAAAGTGG | ACATTACAAG | ACGTTAGCCT | TGAAGTGTAT | 3060 |
| TTAACTGCAC | CAACAGGATG | TATAAAAAAA | CATGGATATA | CAGTGGAAGT | GCAGTTTGAT | 3120 |
| GGAGACATAT | GCAATACAAT | GCATTATACA | AACTGGACAC | ATATATATAT | TTGTGAAGAA | 3180 |
| GCATCAGTAA | CTGTGGTAGA | GGGTCAAGTT | GACTATTATG | GTTATATTA | TGTTCATGAA | 3240 |
| GGAATACGAA | CATATTTTGT | GCAGTTTAAA | GATGATGCAG | AAAAATATAG | TAAAAATAAA | 3300 |
| GTATGGGAAG | TTCATGCGGG | TGGTCAGGTA | ATATTATGTC | CTACATCTGT | GTTAGCAGC | 3360 |
| AACGAAGTAT | CCTCTCCTGA | AATTATTAGG | CAGCACTTGG | CCAACCACCC | CGCCGCGACC | 3420 |
| CATACCAAAG | CCGTCGCCTT | GGGCACCGAA | GAAACACAGA | CGACTATCCA | GCGACCAAGA | 3480 |
| TCAGAGCCAG | ACACCGGAAA | CCCCTGCCAC | ACCACTAAGT | TGTTGCACAG | AGACTCAGTG | 3540 |
| GACAGTGCTC | CAATCCTCAC | TGCATTTAAC | AGCTCACACA | AAGGACGGAT | TAACTGTAAT | 3600 |
| AGTAACACTA | CACCCATAGT | ACATTAAAA | GGTGATGCTA | ATACTTTAAA | ATGTTAAGA | 3660 |
| TATAGATTTA | AAAAGCATTG | TACATTGTAT | ACTGCAGTGT | CGTCTACATG | GCATTGGACA | 3720 |
| GGACATAATG | TAAAACATAA | AAGTGCAATT | GTTACACTTA | CATATGATAG | TGAATGGCAA | 3780 |
| CGTGACCAAT | TTTTGTCTCA | AGTTAAAATA | CCAAAAACTA | TTACAGTGTC | TACTGGATTT | 3840 |
| ATGTCTATAT | GACAAATCTT | GATACTGCAT | CCACAACATT | ACTGGCGTGC | TTTTTGCTTT | 3900 |
| GCTTTGTGTG | CTTTTGTGTG | TCTGCCTATT | AATACGTCCG | CTGCTTTTGT | CTGTGTCTAC | 3960 |
| ATACACATCA | TTAATAATAT | TGGTATTACT | ATTGTGGATA | ACAGCAGCCT | CTGCGTTTAG | 4020 |
| GTGTTTTATT | GTATATATTA | TATTTGTTTA | TATACCATTA | TTTTAATAC | ATACACATGC | 4080 |
| ACGCTTTTTA | ATTACATAAT | GTATATGTAC | ATAATGTAAT | TGTTACATAT | AATTGTTGTA | 4140 |
| TACCATAACT | TACTATTTTT | TCTTTTTTAT | TTTCATATAT | AATTTTTTTT | TTGTTTGTT | 4200 |
| TGTTTGTTTT | TTAATAAACT | GTTATTACTT | AACAATGCGA | CACAAACGTT | CTGCAAAACG | 4260 |
| CACAAAACGT | GCATCGGCTA | CCCAACTTTA | TAAACATGC | AAACAGGCAG | GTACATGTCC | 4320 |
| ACCTGACATT | ATACCTAAGG | TTGAAGGCAA | AACTATTGCT | GAACAAATAT | TACAATATGG | 4380 |
| AAGTATGGGT | GTATTTTTG | GTGGGTTAGG | AATTGGAACA | GGGTCGGGTA | CAGGCGGACG | 4440 |
| CACTGGGTAT | ATTCCATTGG | GAACAAGGCC | TCCCACAGCT | ACAGATACAC | TTGCTCCTGT | 4500 |
| AAGACCCCCT | TTAACAGTAG | ATCCTGTGGG | CCCTTCTGAT | CCTTCTATAG | TTTCTTTAGT | 4560 |
| GGAAGAAACT | AGTTTTATTG | ATGCTGGTGC | ACCAACATCT | GTACCTTCCA | TTCCCCCAGA | 4620 |
| TGTATCAGGA | TTTAGTATTA | CTACTTCAAC | TGATACCACA | CCTGCTATAT | AGATATTAA | 4680 |
| TAATACTGTT | ACTACTGTTA | CTACACATAA | TAATCCCACT | TTCACTGACC | CATCTGTATT | 4740 |
| GCAGCCTCCA | ACACCTGCAG | AAACTGGAGG | GCATTTTACA | CTTTCATCAT | CCACTATTAG | 4800 |
| TACACATAAT | TATGAAGAAA | TTCCTATGGA | TACATTATT | GTTAGCACAA | ACCCTAACAC | 4860 |
| AGTAACTAGT | AGCACACCCA | TACCAGGGTC | TCGCCCAGTG | GCACGCCTAG | GATTATATAG | 4920 |
| TCGCACAACA | CAACAGGTTA | AAGTTGTAGA | CCCTGCTTTT | GTAACCACTC | CCACTAAACT | 4980 |
| TATTACATAT | GATAATCCTG | CATATGAAGG | TATAGATGTG | GATAATACAT | TATATTTTC | 5040 |

```
TAGTAATGAT AATAGTATTA ATATAGCTCC AGATCCTGAC TTTTTGGATA TAGTTGCTTT    5100
ACATAGGCCA GCATTAACCT CTAGGCGTAC TGGCATTAGG TACAGTAGAA TTGGTAATAA    5160
ACAAACACTA CGTACTCGTA GTGGAAAATC TATAGGTGCT AAGGTACATT ATTATTATGA    5220
TTTAAGTACT ATTGATCCTG CAGAAGAAAT AGAATTACAA ACTATAACAC CTTCTACATA    5280
TACTACCACT TCACATGCAG CCTCACCTAC TTCTATTAAT AATGGATTAT ATGATATTTA    5340
TGCAGATGAC TTTATTACAG ATACTTCTAC AACCCCGGTA CCATCTGTAC CCTCTACATC    5400
TTTATCAGGT TATATTCCTG CAAATACAAC AATTCCTTTT GGTGGTGCAT ACAATATTCC    5460
TTTAGTATCA GGTCCTGATA TACCCATTAA TAATAACTGAC CAAGCTCCTT CATTAATTCC    5520
TATAGTTCCA GGGTCTCCAC AATATACAAT TATTGCTGAT GCAGGTGACT TTTATTTACA    5580
TCCTAGTTAT TACATGTTAC GAAAACGACG TAAACGTTTA CCATATTTTT TTCAGATGT     5640
CTCTTTGGCT GCCTAGTGAG GCCACTGTCT ACTTGCCTCC TGTCCCAGTA TCTAAGGTTG    5700
TAAGCACGGA TGAATATGTT GCACGCACAA ACATATATTA TCATGCAGGA ACATCCAGAC    5760
TACTTGCAGT TGGACATCCC TATTTTCCTA TTAAAAAACC TAACAATAAC AAAATATTAG    5820
TTCCTAAAGT ATCAGGATTA CAATACAGGG TATTTAGAAT ACATTTACCT GACCCCAATA    5880
AGTTTGGTTT TCCTGACACC TCATTTTATA ATCCAGATAC ACAGCGGCTG GTTGGGCCT    5940
GTGTAGGTGT TGAGGTAGGT CGTGGTCAGC CATTAGGTGT GGGCATTAGT GGCCATCCTT    6000
TATTAAATAA ATTGGATGAC ACAGAAAATG CTAGTGCTTA TGCAGCAAAT GCAGGTGTGG    6060
ATAATAGAGA ATGTATATCT ATGGATTACA AACAAACACA ATTGTGTTTA ATTGGTTGCA    6120
AACCACCTAT AGGGGAACAC TGGGGCAAAG GATCCCCATG TACCAATGTT GCAGTAAATC    6180
CAGGTGATTG TCCACCATTA GAGTTAATAA ACACAGTTAT TCAGGATGGT GATATGGTTC    6240
ATACTGGCTT TGGTGCTATG GACTTTACTA CATTACAGGC TAACAAAAGT GAAGTTCCAC    6300
TGGATATTTG TACATCTATT TGCAAATATC CAGATTATAT TAAAATGGTG TCAGAACCAT    6360
ATGGCGACAG CTTATTTTTT TATTTACGAA GGGAACAAAT GTTTGTTAGA CATTTATTTA    6420
ATAGGGCTGG TACTGTTGGT GAAAATGTAC CAGACGATTT ATACATTAAA GGCTCTGGGT    6480
CTACTGCAAA TTTAGCCAGT TCAAATTATT TTCCTACACC TAGTGGTTCT ATGGTTACCT    6540
CTGATGCCCA AATATTCAAT AAACCTTATT GGTTACAACG AGCACAGGGC CACAATAATG    6600
GCATTTGTTG GGGTAACCAA CTATTTGTTA CTGTTGTTGA TACTACACGC AGTACAAATA    6660
TGTCATTATG TGCTGCCATA TCTACTTCAG AAACTACATA TAAAAATACT AACTTTAAGG    6720
AGTACCTACG ACATGGGGAG GAATATGATT TACAGTTTAT TTTTCAACTG TGCAAAATAA    6780
CCTTAACTGC AGACGTTATG ACATACATAC ATTCTATGAA TTCCACTATT TTGGAGGACT    6840
GGAATTTTGG TCTACAACCT CCCCCAGGAG GCACACTAGA AGATACTTAT AGGTTTGTAA    6900
CCCAGGCAAT TGCTTGTCAA AAACATACAC CTCCAGCACC TAAAGAAGAT GATCCCCTTA    6960
AAAAATACAC TTTTTGGGAA GTAAATTTAA AGGAAAAGTT TTCTGCAGAC CTAGATCAGT    7020
TTCCTTTAGG ACGCAAATTT TTACTACAAG CAGGATTGAA GGCCAAACCA AAATTTACAT    7080
TAGGAAAACG AAAAGCTACA CCCACCACCT CATCTACCTC TACAACTGCT AAACGCAAAA    7140
AACGTAAGCT GTAAGTATTG TATGTATGTT GAATTAGTGT TGTTTGTTGT GTATATGTTT    7200
GTATGTGCTT GTATGTGCTT GTAAATATTA AGTTGTATGT GTGTTTGTAT GTATGGTATA    7260
ATAAACACGT GTGTATGTGT TTTTAAATGC TTGTGTAACT ATTGTGTCAT GCAACATAAA    7320
TAAACTTATT GTTTCAACAC CTACTAATTG TGTTGTGGTT ATTCATTGTA TATAAACTAT    7380
ATTTGCTACA TCCTGTTTTT GTTTTATATA TACTATATTT TGTAGCGCCA GGCCCATTTT    7440
```

```
GTAGCTTCAA CCGAATTCGG TTGCATGCTT TTTGGCACAA AATGTGTTTT TTTAAATAGT      7500

TCTATGTCAG CAACTATGGT TTAAACTTGT ACGTTCCTG  CTTGCCATGC GTGCCAAATC      7560

CCTGTTTTCC TGACCTGCAC TGCTTGCCAA CCATTCCATT GTTTTTACA  CTGCACTATG      7620

TGCAACTACT GAATCACTAT GTACATTGTG TCATATAAAA TAAATCACTA TGCGCCAACG      7680

CCTTACATAC CGCTGTTAGG CACATATTTT TGGCTTGTTT TAACTAACCT AATTGCATAT      7740

TTGGCATAAG GTTTAAACTT CTAAGGCCAA CTAAATGTCA CCCTAGTTCA TACATGAACT      7800

GTGTAAAGGT TAGTCATACA TTGTTCATTT GTAAAACTGC ACATGGGTGT GTGCAAACCG      7860

ATTTTGGGTT ACACATTTAC AAGCAACTTA TATAATAATA CTAA                       7904
```

( 2 ) INFORMATION FOR SEQ ID NO:3:

( i ) SEQUENCE CHARACTERISTICS:
        ( A ) LENGTH: 162 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( x i ) SEQUENCE DESCRIPTION: SEQ ID NO:3:

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

Ile Ile Leu Glu Cys Val Tyr Cys Lys Gln Gln Leu Leu Arg Arg Glu
        35                  40                  45

Val Tyr Asp Phe Ala Phe Arg Asp Leu Cys Ile Val Tyr Arg Asp Gly
    50                  55                  60

Asn Pro Tyr Ala Val Cys Asp Lys Cys Leu Lys Phe Tyr Ser Lys Ile
65                  70                  75                  80

Ser Glu Tyr Arg His Tyr Cys Tyr Ser Leu Tyr Gly Thr Thr Leu Glu
                85                  90                  95

Gln Gln Tyr Asn Lys Pro Leu Cys Asp Leu Leu Ile Arg Cys Ile Asn
            100                 105                 110

Cys Gln Lys Pro Leu Cys Pro Glu Glu Lys Gln Arg His Leu Asp Lys
        115                 120                 125

Lys Gln Arg Phe His Asn Ile Arg Gly Arg Trp Thr Gly Arg Cys Met
    130                 135                 140

Ser Cys Cys Arg Ser Ser Arg Thr Arg Arg Glu Thr Gln Leu Xaa Ser
145                 150                 155                 160

Cys Met
```

( 2 ) INFORMATION FOR SEQ ID NO:4:

( i ) SEQUENCE CHARACTERISTICS:
        ( A ) LENGTH: 162 amino acids
        ( B ) TYPE: amino acid
        ( C ) STRANDEDNESS: Not Relevant
        ( D ) TOPOLOGY: Not Relevant ( i i ) MOLECULE TYPE: protein ( i i i ) HYPOTHETICAL: NO ( x i ) SEQUENCE DESCRIPTION: SEQ ID NO:4:

```
Met His Gln Lys Arg Thr Ala Met Phe Gln Asp Pro Gln Glu Arg Pro
```

|     | 1   |     |     | 5   |     |     |     |     | 10  |     |     |     |     | 15  |     |
| --- | --- | --- | --- | --- | --- | --- | --- | --- | --- | --- | --- | --- | --- | --- | --- |
| Arg | Lys | Leu | Pro 20 | Gln | Leu | Cys | Thr | Glu 25 | Leu | Gln | Thr | Thr | Ile 30 | His | Asp |
| Ile | Ile | Leu 35 | Glu | Cys | Val | Tyr | Cys 40 | Lys | Gln | Gln | Leu | Leu 45 | Arg | Arg | Glu |
| Val | Tyr 50 | Asp | Phe | Ala | Phe | Arg 55 | Asp | Leu | Cys | Ile | Val 60 | Tyr | Arg | Asp | Gly |
| Asn 65 | Pro | Tyr | Ala | Val | Cys 70 | Asp | Lys | Cys | Leu | Lys 75 | Phe | Tyr | Ser | Lys | Ile 80 |
| Ser | Glu | Tyr | Arg | His 85 | Tyr | Cys | Tyr | Ser | Val 90 | Tyr | Gly | Thr | Thr | Leu 95 | Glu |
| Gln | Gln | Tyr | Asn 100 | Lys | Pro | Leu | Cys | Asp 105 | Leu | Leu | Ile | Arg | Cys 110 | Ile | Asn |
| Cys | Gln | Lys 115 | Pro | Leu | Cys | Pro | Glu 120 | Glu | Lys | Gln | Arg | His 125 | Leu | Asp | Lys |
| Lys | Gln 130 | Arg | Phe | His | Asn | Ile 135 | Arg | Gly | Arg | Trp | Thr 140 | Gly | Arg | Cys | Met |
| Ser 145 | Cys | Cys | Arg | Ser | Ser 150 | Arg | Thr | Arg | Arg | Glu 155 | Thr | Gln | Leu | Xaa | Ser 160 |
| Cys | Met |     |     |     |     |     |     |     |     |     |     |     |     |     |     |

METHODS AND A DIAGNOSTIC AID FOR DISTINGUISHING A SUBSET OF HPV THAT IS ASSOCIATED WITH AN INCREASED RISK OF DEVELOPING CERVICAL DYSPLASIA AND CERVICAL CANCER

This application is a Continuation-In-Part application of U.S. Ser. No. 08/127,906 filed Sep. 28, 1993, now abandoned.

BACKGROUND OF THE INVENTION

The present invention relates to methods and a diagnostic aid for distinguishing a subset of HPV that is associated with an increased risk of developing cervical dysplasia and cervical cancer.

Human papillomavirus (HPV) has been identified previously as an important cofactor in the development of cervical neoplasia and cancer. Infection with HPV is however insufficient to cause cervical cancer. That is to say that when conducting random surveys 30–50% of all women are infected with HPV but only 8/100,000 women ever develop cervical cancer. This can in part be explained by the fact that women are often treated for precursor dysplastic cervical disease detected at annual Pap smear. Despite the existence of Pap smear screening, epidemiologic investigations continue to implicate HPV as the single greatest risk factor for progression to cervical dysplasia and cancer.

Many investigations continue to search for host and/or viral (HPV) markers that will help identify those women infected with HPV who are at risk for cervical dysplasia or invasive cervical cancer. Specific host genetics in the HLA Class II locus have been one area recently identified in a subset of patients infected with HPV. Individuals infected with HPV-16 who have specific HLA haplotypes will either be at risk or protected from getting cervical cancer. In this case it has been possible to identify genetic markers that predispose a patient with HPV to progress to cancer.

There are probably many different pathways that result in the manifestation of cervical cancer. There is a 5–10% subset of cervical cancer which is in fact negative for HPV but which may be associated with p53 mutations.

Another reasonable area to look for markers of increased risk for HPV-16 associated cancers is to investigate viral genes. The HPV-16 E6 and E7 gene products are known by themselves to induce in vitro transformation. Both E6 and E7 interact with host cell cycle regulatory elements.

It is therefore an object of the present invention to be able to provide such a marker of increased risk for cancers associated with HPV-16.

SUMMARY OF THE INVENTION

The methods of the present invention and the diagnostic aid of distinguishing a subset of HPV that is associated with an increased risk of developing cervical dysplasia and cervical cancer is characterized either by distinguishing valine from leucine at amino acid position 83 of the expression product of the HPV-16 E6 open reading frame (SEQ ID NOS: 3 and 4), or by distinguishing a nucleotide difference of G (Guanine) or T (Thymidine) at nt 350 in the HPV-16 E6 gene (SEQ ID NOS: 1 and 2). Protein or DNA for these analyses is obtained from patient cells or tissue samples.

BRIEF DESCRIPTION OF THE DRAWINGS

FIGS. 2A–2H show the reference nucleotide sequence for HPV-16 E6 (SEQ ID NO: 1).

FIGS. 3A–3H show the variant nucleotide sequence for HPV-16 E6 (SEQ ID NO: 2).

FIG. 4 shows a reference HPV-16 E6 protein sequence (SEQ ID NO: 3); and

FIG. 5 shows a variant HPV-16 E6 protein sequence (SEQ ID NO: 4) The variation is marked at amino acid position 83 (amino acid position 90 of SEQ ID NO: 4).

Figure 1:
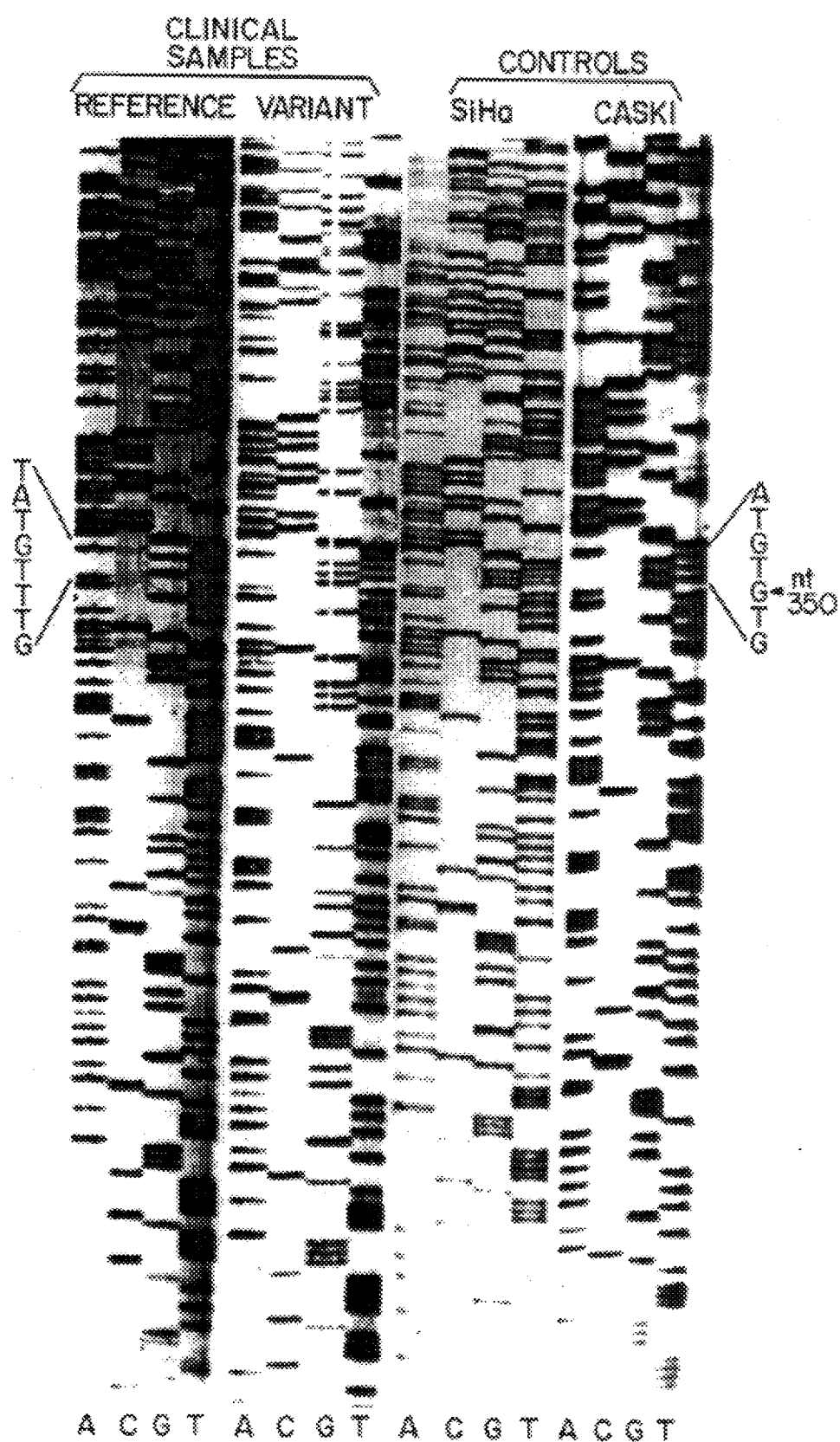
FIG. 1 shows examples of DNA sequencing gels specifically locating the nucleotide 350 HPV-16 E6 protein variant and reference sequences; three variant sequences are shown, one referred to as "Variant" that is from a representative clinical sample, and two additional variants labeled SiHa and Caski; these designations (Siha, Caski) are the actual names assigned to these cell lines derived from cervical carcinoma cells.

The papillomavirus E6 and E7 open reading frames (ORF's) have been implicated in the induction and maintenance of cervical neoplasia. The E6 and E7 ORF's are commonly transcribed into mRNA and the respective proteins have been identified in clinical specimens and cell lines derived from cervical carcinomas (i.e. SiHa, Caski). These genes from oncogenic HPV's possess transforming potential in vitro and their expression has been shown to be required for the maintenance of the transformed and malignant phenotype of cervical cancer cells. The HPV-16 E6 protein has been shown to complex with and degrade the cellular p53 protein in vitro by a ubiquitin-dependent proteolysis pathway. The HPV E7 protein has been shown to complex with pRB, a cellular phosphoprotein important in regulating the cell cycle. HPV type 16 is the most commonly identified HPV which is present in 50–90% of cervical carcinomas. To identify specific viral sequence changes potentially associated with oncogenicity, the complete nucleotide (nt) sequence of HPV-16 E6 and E7 ORF's was evaluated in clinical specimens. Although variation in these genes has been previously reported (Icenogle et al) and the potential that changes in these genes may be relevant has been suggested, no such direct evidence has been previously reported. Specifically, no nucleotide changes or amino acid changes in the HPV-16 E6 or E7 gene or protein have been associated with cervical dysplasia or cervical cancer.

During a series of HPV research studies, approximately 3,000 cervical swab samples were collected from women attending clinics at the University of New Mexico in Albuquerque. Pap smears were collected at the time of the clinic visit. Cervical swabs were aliquoted, digested and ethanol precipitated. Samples were screened for HPV DNA using both the ViraPap dot blot assay (Digene Diagnostics) and the L1 consensus PCR method of Manos et al. Within the constraints of the HPV detection systems applied, 143 samples contained HPV-16 only. Forty-six of these samples, representing various levels of cervical disease, were selected for DNA sequencing in this study.

HPV-16 DNA's were amplified from clinical tissue samples using a PCR amplification system developed by Michele Manos et al. The primer pair TYN07/WD76, produces a 1,250 base-pair PCR product. This fragment spans the E6-E7 and part of the E1 open reading frames of HPV-16. Resultant PCR products were gel purified (GeneClean II), immobilized as single-stranded templates (via a solid phase magnetic separation technique) and directly sequenced by the dideoxy chain-termination method (Sequenase 2.0) with internal type specific primers and sulfur 35.

Forty-six clinical samples positive for HPV-16 DNA were amplified and sequenced from nucleotide (nt) 100 through nt 880. Twenty-nine of 46 (63%) of the samples exhibited sequence variation when compared to the reference HPV-16 sequence (GENBANK) (see FIGS. 2A–2H, Reference Nucleotide Sequence, (SEQ ID NO: 1). The position of nt sequence changes are shown in Table 1. Of the 29 samples containing HPV-16 E6 and E7 nt changes, 27 (97%) showed amino acid residue changes (Table 2). Twenty-four of the 29 nt variants (83%) exhibited a change at nt position 350. This change for SiHa, Caski and a representative clinical sample is shown in Table 1. This T to G change resulted in a leucine to valine substitution in the E6 ORF at amino acid residue 83 (amino acid residue 90 in SEQ ID NO: 3). SiHa and Caski cell lines also contained this change. Other variants (n=5) are shown in Table 2. Seventeen of the 46 (37%) samples sequenced were identical to the reference HPV-16 sequence. As indicated, a significant association was observed among Pap smears and HPV-16 nt 350 variants, in that women infected with the nt 350 variant were more likely to present with higher grade Pap smear results than women with the reference strain HPV-16 (see Table 3).

TABLE 1

| | HPV16 Nucleotide Sequence Variants | | | | | | | | | | | | | |
|---|---|---|---|---|---|---|---|---|---|---|---|---|---|---|
| | | | | E6 | ORF | | | | | | | E7 | ORF | |
| A.A. Residue | 10 | 14 | 28 | 28 | 61 | 62 | 78 | 83 | 114 | 133 | 143 | 28 | 57 | 78 |
| Nucleotide | 131 | 145 | 185 | 187 | 286 | 289 | 335 | 350 | 442 | 502 | 532 | 645 | 732 | 795 |
| CONTROL | | | | | | | | | | | | | | |
| Reference pph 16 | A | G | T | A | T | A | C | T | A | C | A | A | T | T |
| SiHa | | | | | | | | G | C | | | C | | |
| Caski | | | | | | | | G | | | | | | |
| 16 plasmid | | | | | | | | | | | | | | |
| CANCER | | | | | | | | | | | | | | |
| 151BHQ | | | | G | | | | | | | | | | |
| 993 | | | | | | G | | | | | | | | |
| 990 | | | | | | G | | | | | | | | |
| 987 | G | | | | | G | | | | | | | | |
| CIN III | | | | | | | | | | | | | | |
| J9 | | | | | | | | G | | | | | | |
| T12 | | T | | | | | | | | | | | | |
| T31 | | | | | | | | G | | | | | | |
| T36 | | | | | | | | G | | | | | | |
| T82 | | | | | A | G | T | | | | | | | |
| T96 | | | | | | | | G | | | | | | |
| T190 | | | | | | | | G | | | | | | |
| T193 | | | | | | | | | | | | | | |
| T207 | | | | | | | | | | | | | | |
| T233 | | | | | | | | G | | | | G | C | G |
| T240 | | | | | | | | G | | G | | | | |
| T275 | | | | | | | | G | | | | | | |
| T400 | | | | | | | | G | | | | | | |
| CIN II | | | | | | | | | | | | | | |
| T195 | | | | | | | | G | | | | | | |
| T247 | | | | | | | | | | | | | | |
| T289 | | | | | | | | G | | | | | | |
| T330 | | | | | | | | G | | | | | | |
| T363 | | T | | | | | | G | | | | | | |
| T385 | | | | | | | | G | | | | | | |
| T596 | | | | | | | | G | | | | | | |
| CIN I | | | | | | | | | | | | | | |
| C119 | | | | | | | | G | | | | | | |
| T46 | | | | | | G | | | | | | | | C |
| T177 | | | | | | | | | | | | | | |
| T318 | | | | | | | | | | | | | | |
| U63 | | | | | | | | | | | | | | |
| U74 | | | | | | | | | | | | | | |
| NEGATIVE | | | | | | | | | | | | | | |

TABLE 1-continued

HPV16 Nucleotide Sequence Variants

| Sample | | | | | | |
|---|---|---|---|---|---|---|
| 47-10-11 | | | | | | |
| 4140 | | | | | | |
| J3 | | | | | | |
| S165 | | | | | G | |
| S264 | | | | | | |
| U60 | | | | | | |
| U77 | | | | | | |
| U216 | | | | | | |
| T37 | | | | | | |
| T38 | | | A | G | G | |
| T155 | G | | | | | |
| T165 | | | | | | |
| T338 | | | | | G | |
| T398 | | | | | G | |
| T518 | | | | | | |

CIN = cervical intraepithelial neoplasia
CIN I = mild dysplasia or low grade squamos intraepithelial lesions (LGSIL)

CIN II = moderate dysplasia  
CIN III = severe dyxplasia  } both CIN II and III are considered HGSIL

TABLE 2

HPV-16 Amino Acid Variants

| | E6 ORF | | | | | | | | | | E7 ORF | |
|---|---|---|---|---|---|---|---|---|---|---|---|---|
| A.A. Residue | 10 | 14 | 28 | 61 | 62 | 78 | 83 | 114 | 133 | 143 | 28 | 57 |
| HPV 16 REFERENCE | R | Q | L | A | V | H | L | E | T | S | L | F |
| SiHa | | | | | | | V | D | | | | F |
| CASKI | | | | | | | V | | | | | |
| 16 PLASMID | | | | | | | | | | | | |
| CANCER | | | | | | | | | | | | |
| 151BHQ | | | | | | | | | | | | |
| 993 | | | | | | | V | | | | | |
| 990 | | | | | | | V | | | | | |
| 987 | G | | | | | | V | | | | | |
| CIN III | | | | | | | | | | | | |
| J9 | | | | | | | V | | | | | |
| T12 | | H | | | | | | | | | | |
| T31 | | | | | | | V | | | | | |
| T36 | | | | | | | V | | | | | |
| T82 | | | | | | Y | | | | | | |
| T96 | | | | | | | V | | | | | |
| T190 | | | | | | | V | | | | | |
| T193 | | | | | | | | | | | | |
| T207 | | | | | | | | | | | | |
| T233 | | | | | | | V | | | | | S |
| T240 | | | | | | | V | | | | | |
| T275 | | | | | | | V | | | | | |
| T400 | | | | | | | V | | | | | |
| CIN II | | | | | | | | | | | | |
| T195 | | | | | | | V | | | | | |
| T247 | | | | | | | V | | | | | |
| T289 | | | | | | | | | | | | |
| T330 | | | | | | | V | | | | | |
| T363 | | H | | | | | V | | | | | |
| T385 | | | | | | | V | | | | | |
| T596 | | | | | | | V | | | | | |
| CIN I | | | | | | | | | | | | |
| C119 | | | | | | | V | | | | | |
| T46 | | | | | | | | | | | | |
| T177 | | | | | | | | | | | | |
| T299 | | | | | | | V | | | | | |
| T318 | | | | | | | | | | | | |
| U63 | | | | | | | | | | | | |

TABLE 2-continued

| | HPV-16 Amino Acid Variants | | | | | | | | | | | |
|---|---|---|---|---|---|---|---|---|---|---|---|---|
| | | | | | E6 ORF | | | | | | E7 ORF | |
| A.A. Residue | 10 | 14 | 28 | 61 | 62 | 78 | 83 | 114 | 133 | 143 | 28 | 57 |
| U74 NEGATIVE | | | | | | | | | | | | |
| 4140 | | | | | | | | | | | | |
| 47-10-11 | | | | | | | | | | | | |
| J3 | | | | | | | | | | | | |
| S165 | | | | | | | V | | | | | |
| S264 | | | | | | | | | | | | |
| T37 | | | | | | | | | | | | |
| T38 | | | | | | | V | | | | | |
| T155 | | V | | | | | | | | | | |
| T165 | | | | | | | | | | | | |
| T338 | | | | | | | V | | | | | |
| T398 | | | | | | | | | | | | |
| T518 | | | | | | | | | | | | |
| U60 | | | | | | | | | | | | |
| U77 | | | | | | | | | | | | |
| U216 | | | | | | | | | | | | |

CIN = cervical intraepithelial neoplasia
CIN I = mild dysplasia or low grade squamos intraepithelial lesions (LGSIL)
CIN II = moderate dysplasia
CIN III = severe dysplasia
both CIN II and III are considered HGSIL

TABLE 3

Summary distributions of patient's Pap scores HPV-16 reference type & variants. Data based on 45 HPV-16 samples.

| PAP Score | HPV-16 Reference Type | HPV-16 bp350 Variant | HPV-16 Other Variants |
|---|---|---|---|
| Negative | 10 | 4 | 1 |
| CIN I | 4 | 2 | 1 |
| CIN II | 1 | 6 | 0 |
| CIN III | 2 | 9 | 1 |
| Cancer | 0 | 3 | 1 |
| Total | 17 | 24 | 5 |

CIN = cervical intraepithelial neoplasia
CIN I = mild dysplasia or low grade squamos intraepithelial lesions (LGSIL)
CIN II = moderate dysplasia
CIN III = severe dysplasia
both CIN II and III are considered HGSIL Of the 17 samples that matched the reference strain HPV-16 only 3 (18%) showed high grade squamous intraepithelial lesions (HGSIL). In contrast, 18 of the 24 HPV-16 nt 350 variants (75%) were identified in women presenting with a Pap smear diagnosis of HGSIL (OR=15.0 95% CI2.2–124.2). Thus, this difference in the E6 gene or protein would appear to provide a good diagnostic aid for assessing an increased risk of developing cervical dysplasia, and cervical cancer. Based on data presented as part of this disclosure in Tables 1, 2, and 3, a 15 fold relative risk for HGSIL or cervical cancer is observed when distinguishing between a G or T and nt position 350 in the HPV-16 E6 ORF. Similarly this risk can be distinguished through identification of the corresponding amino acids, leucine or valine at position 83 in the HPV-16 E6 protein (amino acid position 90 of SEQ ID NOS: 3 and 4). This therefore represents a biomarker of risk for developing either HGSIL or invasive cervical cancer associated with HPV-16 when this distinction is made.

With the present invention, a single base change at nt position 350 (see FIGS. 3A–3H, Variant Nucleotide Sequence (SEQ ID NO: 2)) (reference is based on comparison to the HPV-16 ppH 16.GB-Vi sequence in GENBANK (SEQ ID NO: 1)) that is statistically associated with cervical dysplasia has been identified. This variant results in an amino acid change of leucine to valine. The complete amino acid sequence for the HPV-16 E6 Variant and Reference strain are provided (See FIGS. 4 and 5 (SEQ ID NOS: 4 and 3, respectively)). Although the exact function of this variant is not known, it clearly marks an HPV-16 sequence associated with cervical dysplasia and cancer, therefore providing a diagnostic aid for women infected with HPV-16 containing this variant.

Distinguishing the difference of either T or G at nt 350 in the HPV-16 E6 gene can be approached from the level of nucleic acid methodologies or from direct detection of the reference or variant E6 protein, which contains an amino acid of leucine or valine, respectively, at amino acid position 83 in the HPV-16 ORF (amino acid position 90 of SEQ ID NOS: 3 and 4, respectively). It should be noted that cervical or vaginal cells or tissue samples from patients would be the source of material for the methods of this invention.

Nucleic acid methods that can be applied include amplification techniques such as polymerase chain reaction, ligase chain reaction, etc. followed by direct DNA sequencing through the nt 350 region or hybridization with sequence-specific DNA probes. These methods would specifically target the HPV-16 E6 gene and would include nt position 350 of this gene.

In addition, antibody-based tests that distinguish valine or leucine at amino acid position 83 of the HPV-16 E6 proteins (amino acid position 90 of SEQ ID NOS: 3 and 4) are also possible. For example, specific antibodies (monoclonal or polyclonal) to native, expressed or synthetic peptides which would distinguish the valine or leucine at amino acid position 83 and relevant adjacent amino and carboxy residues could be generated and used to detect this amino acid difference. Such methods for detection include standard application of liquid and solid-phase enzyme and radioimmuno assay or in situ-based immunohistochemistry.

In summary, although the aforementioned tests utilized direct DNA sequence analysis of PCR products generated from clinical samples containing HPV-16, all methodologies utilizing nucleotide sequencing, sequence-specific hybridization probes, or antibody/antigen-based assays designed to detect the variation of T to G at nt position 350, which also corresponds to HPV-16 E6 amino acid residue 83, are possible. Therefore, the present invention is, of course, in no way restricted to the specific disclosure of the specification and drawings, but also encompasses any modifications within the scope of the appended claims.

We claim:

1. A method and diagnostic aid to distinguish a subset of HPV that is associated with an increased risk of developing cervical dysplasia or cervical cancer, said method including the steps of:

taking a cervical sample;

preparing said sample to expose HPV-16 E6 gene present in said sample; and detecting whether the nucleotide T or G is present at nt 350 in at least one HPV-16 E6 gene (SEQ ID NOS: 1 and 2) in said prepared sample, wherein the presence of the nucleotide G at nt 350 is associated with an increased risk of developing cervical dysplasia or cervical cancer.

2. A method according to claim 1, wherein said step of detecting comprises using DNA sequence analysis of PCR products generated that include the HPV-16 E6 ORF.

3. A method according to claim 1, wherein said step of detecting comprises using nucleotide sequencing of HPV-16 E6 gene or a portion of this gene that includes nt position 350.

4. A method according to claim 1, wherein said step of detecting comprises using sequence-specific hybridization probes to distinguish a T or G at nt position 350 in the HPV-16 E6 gene (SEQ ID NOS: 1 and 2).

5. A method according to claim 1, wherein said step of detecting comprises direct DNA sequencing through nt 350 of the HPV-16 E6 gene (SEQ ID NOS: 1 and 2).

6. A method according to claim 1, wherein said step of detecting comprises the use of ligase chain reaction.

7. A method and diagnostic aid to distinguish a subset of HPV that is associated with an increased risk of developing cervical dysplasia or cervical cancer, said method including the steps of:

taking a cervical sample;

preparing said sample to expose HPV-16 E6 proteins present in said sample; and detecting whether valine or leucine is present at amino acid position 83 of the expression product of the HPV-16 E6 ORF (amino acid position 90 of SEQ ID NOS: 4 and 3, respectively) in said prepared sample, wherein the presence of valine at amino acid position 83 is associated with an increased risk of developing cervical dysplasia or cervical cancer.

8. A method according to claim 7, wherein said step of detecting comprises an immunoassay.

9. A method according to claim 7, wherein said step of detecting comprises distinguishing between leucine and valine at amino acid position 83 of the HPV-16 E6 ORF (amino acid position90 of SEQ ID NOS: 3 and 4) using antibodies to native, expressed or synthetic HPV-16 E6 peptides.

10. A method according to claim 1, wherein said step of detecting comprises hybridization of said at least one HPV-16 E6 gene with sequence-specific DNA probes.

* * * * *

UNITED STATES PATENT AND TRADEMARK OFFICE
CERTIFICATE OF CORRECTION

PATENT NO. : 5,679,509
DATED : October 21, 1997
INVENTOR(S) : Wheeler et al.

It is certified that error appears in the above-identified patent and that said Letters Patent is hereby corrected as shown below:

Column 1,
Line 10, insert:

-- ACKNOWLEDGEMENT OF FEDERAL RESEARCH SUPPORT

This invention was made, at least in part, with funding from the National Institutes of Health (Grant No. DHHS AI32917). The United States Government has certain rights in this invention. --

Signed and Sealed this

Thirtieth Day of March, 2004

JON W. DUDAS
*Acting Director of the United States Patent and Trademark Office*